US008962333B2

(12) United States Patent
Westpheling et al.

(10) Patent No.: US 8,962,333 B2
(45) Date of Patent: Feb. 24, 2015

(54) RESTRICTION/MODIFICATION POLYPEPTIDES, POLYNUCLEOTIDES, AND METHODS

(75) Inventors: Janet Westpheling, Bogart, GA (US); DaeHwan Chung, Athens, GA (US); Jennifer Huddleston, Abilene, TX (US); Joel A. Farkas, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 242 days.

(21) Appl. No.: 13/439,069

(22) Filed: Apr. 4, 2012

(65) Prior Publication Data

US 2012/0252072 A1  Oct. 4, 2012

Related U.S. Application Data

(60) Provisional application No. 61/471,408, filed on Apr. 4, 2011.

(51) Int. Cl.
*C12N 15/74* (2006.01)
*C12N 9/22* (2006.01)
*C12N 9/10* (2006.01)
*C12P 19/34* (2006.01)

(52) U.S. Cl.
CPC ............... *C12N 9/22* (2013.01); *C12N 9/1007* (2013.01); *C12P 19/34* (2013.01); *C12Y 201/01037* (2013.01); *C12Y 301/21004* (2013.01)
USPC ..................... 435/471; 435/252.3; 435/252.1; 435/193

(58) Field of Classification Search
None
See application file for complete search history.

(56) References Cited

U.S. PATENT DOCUMENTS

| | | | | |
|---|---|---|---|---|
| 4,695,546 | A | * | 9/1987 | Aiba et al. ..................... 435/485 |
| 5,068,194 | A | * | 11/1991 | Imanaka et al. ............ 435/252.5 |
| 5,872,238 | A | | 2/1999 | Weber et al. |
| 8,278,087 | B2 | | 10/2012 | Remmerejt et al. |
| 8,420,358 | B2 | | 4/2013 | Claassen et al. |
| 8,420,375 | B2 | | 4/2013 | Osterhout et al. |
| 8,435,770 | B2 | | 5/2013 | Hogsett et al. |
| 8,470,566 | B2 | | 6/2013 | Trawick et al. |
| 8,486,687 | B2 | | 7/2013 | Atkinson et al. |
| 8,497,128 | B2 | | 7/2013 | VanKranenburg et al. |
| 2011/0306089 | A1 | | 12/2011 | Sowers et al. |

OTHER PUBLICATIONS

Accetto et al., "Type II restriction modification systems of *Prevotella bryanti* TC1-1 and *Prevotella ruminicola* 23 strains and their effect on the efficiency of DNA introduction via electroporation," *FEMS Microbiol. Lett.*, Jun. 15, 2005; 247(2):177-183.

Bailey et al., "Fitting a mixture model by expectation maximization to discover motifs in biopolymers," *Proc. Int. Conf. Intell Syst. Mol. Biol.*, 1994; 2:28-36.
Bart et al., "Direct detection of methylation in genomic DNA," *Nucleic Acids Res.* 2005; 33(14):e124, pp. 1-6.
Benson et al., "GenBank," *Nucleic Acids Res.* Jan. 2009; vol. 37, Database Issue:D26-D31.
Bista, "Cloning and characterization of a Novel Thermostable Endoglucanase from *Caldicellulosiruptor bescii* in Heterologous Host *Escherichia coli*," Thesis. Tampere University of Technology, Aug. 2011; 74 pages total.
Chen et al., "Factors involved in the transformation of previously non-transformable Clostridium perfringens type B," *FEMS Microbiol. Letters*, Jul. 1996; 140(2-3):185-191.
Chung et al., "Methylation by a Unique α-class N4-Cytosine Methyltransferase is required for DNA Transformation of *Caldicellulosiruptor bescii* DSM6725: Use for Construction of Mutants that affect Biomass Utilization," Genomic Science Awardee Meeting X Feb. 2012; pp. 1-45.
Chung et al., "Identification and characterization of CbeI, a novel thermostable restriction enzyme from *Caldicellulosiruptor bescii* DSM 6725 and a member of a new subfamily of HaeIII-like enzymes," *J Ind. Microbiol. Biotechnol.*, 2011; 38:1867-1877.
Crowe et al., "SeqDoC: rapid SNP and mutation detection by direct comparison of DNA sequence chromatograms," *BMC Bioinformatics*, 2005; 6:133. 12 pages total.
Cue et al., "Genetic manipulation of *Bacillus methanolicus*, a Gram-Positive, Thermotolerant Methylotroph," *Appl. Environ. Microbiol.*, 1997; 63(4):1406-1420.
Donahue et al., "Overcoming the restriction barrier to plasmid transformation of *Helicobacter pylori*," *Mol. Microbiol.*, Sep. 2000; 37(5):1066-74.
Frith et al., "Discovering sequence motifs with arbitrary insertions and deletions," *PLoS Comput. Biol.*, 2008; 4(5):e1000071. 12 pages total.
Gallagher et al., "Genetic dissection of the *Francisella novicida* restriction barrier," *J. Bacteriol.*, 2008; 190(23):7830-7837.
Genbank AJ414670—National Center for Biotechnology Information, GenBank Locus AJ414670, Accession No. AJ414670, Cloning Vector PSET152, Bethesda, MD [May 29, 2014]. Retrieved from the Internet: URL: www.ncbi.nlm.nih.gov; 3 pgs.
Genbank AF016889—National Center for Biotechnology Information, GenBank Locus AJ414670, Accession No. AF016889, Cloning Vector pWSK29, complete sequence, Bethesda, MD [May 29, 2014]. Retrieved from the Internet: URL: www.ncbi.nlm.nih.gov; 3 pgs.

(Continued)

*Primary Examiner* — Jim Ketter
(74) *Attorney, Agent, or Firm* — Mueting, Raasch & Gebhardt, P.A.

(57) ABSTRACT

The present invention relates to the discovery of a novel restriction/modification system in *Caldicellulosiruptor bescii*. The discovered restriction enzyme is a HaeIII-like restriction enzyme that possesses a thermophilic activity profile. The restriction/modification system also includes a methyltransferase, M.CbeI, that methylates at least one cytosine residue in the CbeI recognition sequence to $m^4C$. Thus, the invention provides, in various aspects, isolated CbeI or M.CbeI polypeptides, or biologically active fragments thereof; isolated polynucleotides that encode the CbeI or M.CbeI polypeptides or biologically active fragments thereof, including expression vectors that include such polynucleotide sequences; methods of digesting DNA using a CbeI polypeptide; methods of treating a DNA molecule using a M.CbeI polypeptide; and methods of transforming a *Caldicellulosiruptor* cell.

7 Claims, 9 Drawing Sheets

(56) References Cited

OTHER PUBLICATIONS

Hethke et al. "A cell-free transcription system for the hyperthermophilic archaeon Pyroccus furiosus," *Nucleic Acids Res.* Jun. 15, 1996; 24(12):2369-76.

Jennert et al., "Gene transfer to *Clostridium cellulolyticum* ATCC 35319," *Microbiology*, 2000;146:3071-3080.

Kataeva et al., "Genome sequence of the anaerobic, thermophilic, and cellulolytic bacterium, *"Anaerocellum thermophilum"* DSM 6725," *J. Bacteriol.*, Jun. 2009; 191(11):3760-3761.

Klimasauskas et al., "Sequence motifs characteristics of DNA[cytosine-N4] methyltransferases: similarity to adenine and cytosine-C5 DNA-methylases," *Nucleic Acids Res.* 1989; 17(23):9823-9832.

Kong et al., "Functional analysis of putative restriction-modification system genes in the *Helicobacter pylori* J99 genome," *Nucleic Acids Res.* 2000. 28(17):3216-3223.

Larkin et al., "Clustal W and Clustal X version 2.0," *Bioinformatics*, 2007; 23(21):2947-2948.

Lynd et al., "Microbial cellulose utilization: fundamentals and biotechnology," *Microbiol. Mol. Biol. Rev.*, 2002; 66(3):506-577.

Malone et al., "Structure-guided analysis reveals nine sequence motifs conserved among DNA amino-methyltransferases, and suggests a catalytic mechanism for these enzymes," *J. Mol. Biol.*, Nov. 3, 1995; 253(4):618-32.

Marchler-Bauer et al., CDD: specific functional annotation with the Conserved Domain Database, *Nucleic Acids Res.* 2009; 37(Database issue):D205-D210. 6 pages total.

Middleton et al., "Specific fragments of phi X174 deoxyribonucleic acid produced by a restriction enzyme from *Haemophilus aegyptius*, endonuclease Z," *J. Virol*, 1972; 10(1):42-50.

Nobusato et al., "Diversity of restriction-modification gene homologues in *Helicobacter pylori*," Dec. 23, 2000; 259(1-2):89-98.

Nölling et al. "Characterization of the archaeal, plasmid-encoded Type II restriction-modification system *Mth*TI from *Methanobacterium thermoformicicum* THF: Homology to the bacterial *Ngo*PII system from *Neisseria gonorrhoeae*," *J. Bacteriol.*, 1992; 174(17):5719-5726.

Orlowski et al., "Structural and evolutionary classification of Type II restriction enzymes based on theoretical and experimental analysis," *Nucleic Acids Res.*, 2008; 36(11):3552-3569.

O'Sullivan et al. "Rapid Mini-Prep Isolation of High-Quality Plasmid DNA from *Lactococcus* and *Lactobacillus* sup.," *Appl. Environ. Microbiol.*, 1993; 59(8):2730-2733.

Page, "Tree view: an application to display phylogenetic trees on personal computers," *Comut Appl Biosci.*, Aug. 1996; 12(4):357-8.

Prangishvili et al., "A restriction endonuclease SuaI from the thermoacidophilic archaebacterium Sulfolobus acidocaldarius," *FEBS Lett.*, Nov. 11, 1985; 192(1):57-60.

Purdy et al., "Conjugative transfer of clostridial shuttle vectors from *Escherichia coli* to Clostridium difficile through circumvention of the restriction barrier," *Mol. Microbiol.* Oct. 2002; 46(2):439-452.

Rao et al., "Direct visualization of site-specific and strand-specific DNA methylation patterns in automated DNA sequencing data," *Nucleic Acids Res.*, 1998; 26(10):2505-2507.

Rasko et al., "BspRI restriction endonuclease: cloning, expression in *Escherichia coli* and sequential cleavage mechanism," *Nucleic Acids Res.*, 2010; 38(20):7155-7166.

Roberts et al., "REBASE—a database for DNA restriction and modification: enzymes, genes and genomes," *Nucleic Acids Res.* 2010; 38(Database Issue):D234-D236.

Rocha et al., "Evolutionary role of restriction/modification systems as revealed by comparative genome analysis," 2001; 11(6):946-958.

Samuelson et al., "Directed evolution of Restriction endonuclease *Bst*YI to Achieve Increased Substrate specificity" *J Mol. Biol.*, 2002; 319(3):673-83.

Sedmak et al. "A rapid, sensitive, and versatile assay for protein using Coomassie brilliant blue G250," *Anal. Biochem.*, May 1, 1977; 79(1-2):544-52.

Svetlichnyi et al., "Anaerocellum thermophilum, new genus new species, an extremely thermophilic cellulolytic eubacterium isolated from hot springs in the valley of geysers (Russian SFSR, USSR)," *Mikrobiologiya*, 1990; 59:598-604.

Wang et al., "Construction of versatile low-copy-number vectors for cloning, sequencing and gene expression in *Escherichia coli*," *Gene*, Apr. 1991; 100:195-9.

Yang et al., "Efficient degradation of lignocellulosic plant biomass, without pretreatment, by the thermophilic anaerobe *Anaerocellum thermophilum*, DSM 6725," *Appl. Environ. Microbiology*, 2009; 75(14):4762-4769.

Yang et al., "Classification of *Anaerocellum thermophilum*' strain DSM 6725 as *Caldicellulosiruptor bescii* sp. nov.," *Intl. J. of Syst. Evol. Microbiology*, 2010; 60:2011-2015.

Zabaznaya et al., "Site-specific endonuclease NspLKI is an isoschizomer of endonuclease HaeIII," *Biochemistry*, Feb. 1999; 64(2):189-193.

International Search Report, mailed Feb. 27, 2013, Patent Application No. PCT US2012/040700, filed Jun. 4, 2012; 4 pgs.

Written Opinion mailed Feb. 27, 2013, Patent Application No. PCT US2012/040700, filed Jun. 4, 2012; 5 pgs.

* cited by examiner

Figure 5

RESTRICTION/MODIFICATION POLYPEPTIDES, POLYNUCLEOTIDES, AND METHODS

CROSS-REFERENCE TO RELATED APPLICATION

This application claims priority to U.S. Provisional Patent Application Ser. No. 61/471,408, filed Apr. 4, 2011, which is incorporated herein by reference in its entirety.

GOVERNMENT FUNDING

The present invention was made with government support under Grant No. DE-AC05-000R22725, awarded by the U.S. Department of Energy, BioEnergy Science Center. The Government has certain rights in this invention.

BACKGROUND

*Caldicellulosiruptor bescii* DSM 6725 (formerly *Anaerocellum thermophilum*, Yang et al. 2009, hit J Syst Evol Microbiol 60:2011-2015) grows at temperatures up to about 90° C. and is the most thermophilic cellulolytic bacterium known. This obligate anaerobe is capable of degrading lignocellulosic biomass including hardwood (e.g., poplar) and grasses with both low lignin (e.g., napier grass and beiniuda grass) and high lignin (e.g., switchgrass) content without chemical pretreatment (Yang et al., 2009 Appl Environ Microbiol 75:4762-4769). When grown on crystalline cellulose, it produces lactate, ethanol, acetate, $H_2$, and $CO_2$ (Svetlichnyi et al., 1990 Mikrobiologiya 59:598-604). Its genome includes sequences encoding cellulases, glycoside hydrolases, pectinases, pullulanases, and transporters that are important in biomass deconstruction (Kataeva et al., 2009 J Bacteriol 191: 3760-3761). This variety of cellulolytic enzymes and end products, in combination with an optimal growth temperature near 80° C. make *C. bescii* an important microorganism not only in the study of biomass deconstruction, but also in the industrial development of ethanol and other biofuels. This genus has many advantages for consolidated bioprocessing (CBP) and offers the possibility for production of bioenergy and bioproducts from lignocellulosic biomass by a single organism in a single step fermentation (Lynd et al., 2002 Microbiol Mol Biol Rev 66:506-577).

SUMMARY OF THE INVENTION

In one aspect, the invention provides an isolated polynucleotide comprising the coding region of Cbes 2438. In some cases, the invention can provide a vector that includes such a polynucleotide operably linked to a promoter. In some cases, the invention can provide a cell that includes such a polynucleotide and/or such a vector.

In another aspect, the invention provides an isolated polynucleotide comprising the coding region of Cbes 2437. In some cases, the invention can provide a vector that includes such a polynucleotide operably linked to a promoter. In some cases, the invention can provide a cell that includes such a polynucleotide and/or such a vector.

In another aspect, the invention provides an isolated polypeptide comprising an amino acid sequence encoded by the coding region of Cbes 2438.

In another aspect, the invention provides an isolated polypeptide comprising an amino acid sequence encoded by the coding region of Cbes 2437.

In another aspect, the invention provides a method that generally includes incubating a DNA molecule comprising at least one 5'-GGCC-3' sequence with a CbeI polypeptide under conditions effective for the CbeI polypeptide to digest the DNA at the 5'-GG/CC-3' sequence.

In another aspect, the invention provides a method that generally includes treating a DNA molecule comprising at least one 5'-GGCC-3' sequence with a M.CbeI polypeptide under condition effective for the M.CbeI polypeptide to methylate at least one C residue of the 5'-GGCC-3' sequence.

In another aspect, the invention provides a method that generally includes introducing a polynucleotide into a microbial cell that comprises a thermophile or a hyperthermophile. In some cases, the method can include treating the DNA with a M.CbeI polypeptide under condition effective for the M.CbeI polypeptide to methylate at least one C residue of the DNA.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 5. Amino acid sequence alignment of CbeI with the subgroup identified in FIG. 4. Amino acid identity is shown as shaded areas with the position of the motif within the protein sequence. Motif start site is indicated. Motif 1: 7.0e-220, motif 2 1.9e-278, motif 3 1.6e-185. Subgroup sequences shown are CbeI (SEQ ID NO:36); BhaII (SEQ ID NO:37); HaeIII (SEQ ID NO:38); Hac_1214 (SEQ ID NO:39); Cthe_2319 (SEQ ID NO:40); HPSH_02550 (SEQ ID NO:41); HMPREF0105_0967 (SEQ ID NO:42); Smon_0161 (SEQ ID NO:43); PRU_0937 (SEQ ID NO:44); HMPREF0573_11018 (SEQ ID NO:45); CUY_2194 (SEQ ID NO:46); Bgr_19490 (SEQ ID NO:47); and GOS_4010239 (SEQ ID NO:48).

DETAILED DESCRIPTION OF ILLUSTRATIVE EMBODIMENTS

The present invention relates to the discovery of a novel restriction/modification system in *Caldicellulosiruptor bescii*. The discovered restriction enzyme is a HaeIII-like restriction enzyme that possesses a thermophilic activity profile. The restriction/modification system also includes a methyltransferase, M.CbeI, that methylates at least one inner cytosine residue in the CbeI recognition sequence (5'-GGCC-3') to m$^4$C. Thus, the invention provides, in various aspects, isolated CbeI or M.CbeI polypeptides, or biologically active fragments thereof; isolated polynucleotides that encode the CbeI or M.CbeI polypeptides or biologically active fragments thereof, including expression vectors that include such polynucleotide sequences; methods of digesting DNA using a CbeI polypeptide; methods of treating a DNA molecule using a M.CbeI polypeptide; and methods of transforming a *Caldicellulosiruptor* cell.

Despite prior attempts to directly transform members of the *Caldicellulosiruptor* genus, this is the first report of success. Because members of the genus *Caldicellulosiruptor* possess certain biology properties of potential commercial value (e.g., biomass conversion), the ability to genetically manipulate these organisms can assist in metabolically engineering members of this genus for, for example, their use in consolidated bioprocessing that produces one or more biofuels and/or one or more bioproducts. Thus, certain aspects of the invention can be used to overcome restriction that may assist methods of DNA transformation of *Caldicellulosiruptor* species using DNA from, for example, homologous and/or heterologous sources. Moreover, these aspects may be generalized to permit transformation of other thermophilic and/or hyperthermophilic microbes.

As noted above, *Caldicellulosiruptor bescii* was formerly classified as *Anaerocellum thermophilum*. The genome of *C. bescii* was originally annotated when the organism was known as *A. thermophilum*. The annotations were modified upon reclassification of the organism to replace Athe annotations with Cbes annotations, reflecting the reclassification of the organism. Neither the substantive content of the annotation nor the numerical portion of the annotations changed. Thus, for example, the original annotation Athe 2438 is now referred to as Cbes 2438. Nevertheless, Athe annotations and Cbes annotations may be used interchangeably.

Figure 1:
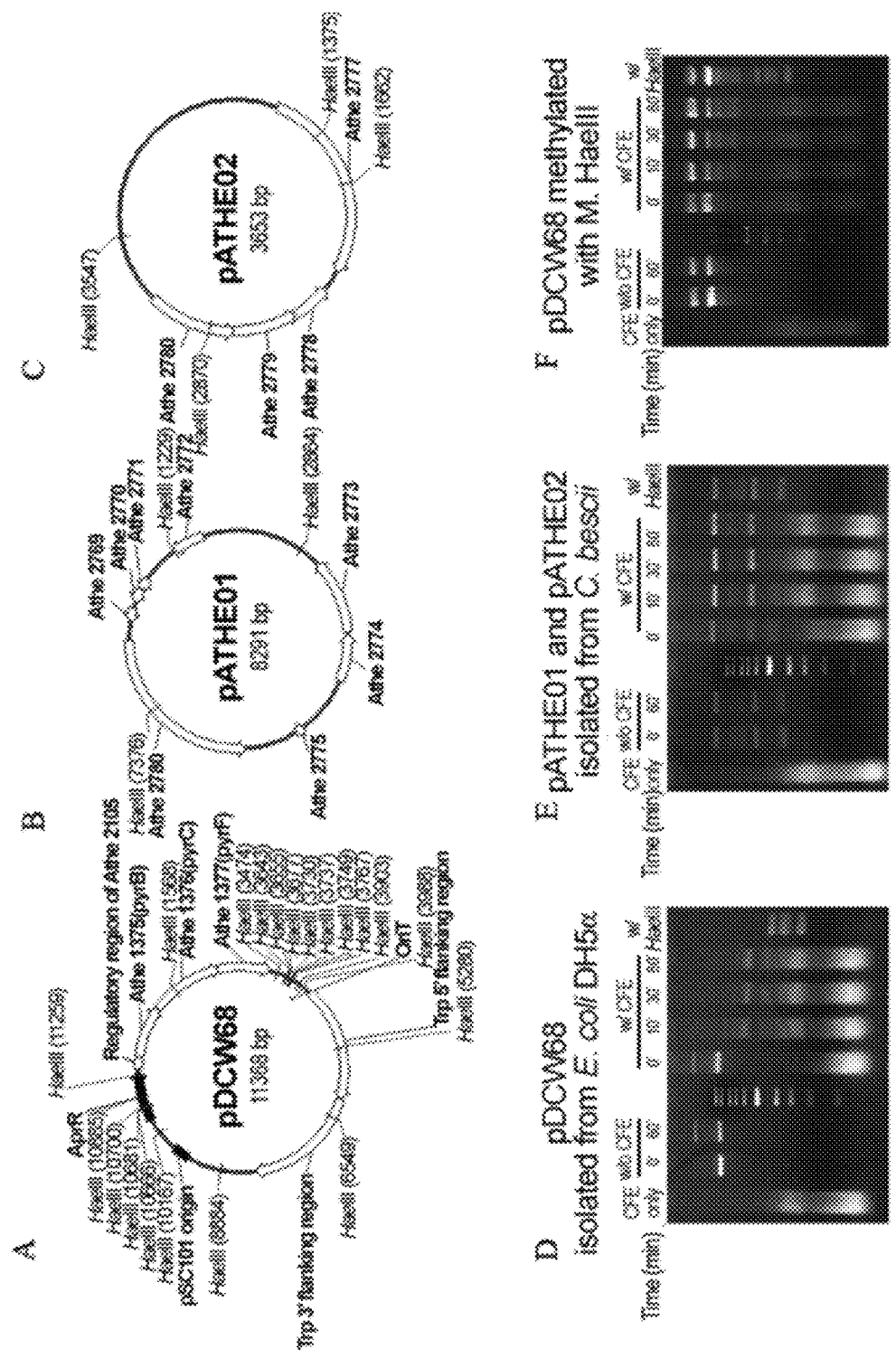
FIG. 1. Detection of a HaeIII-like restriction/modification system in *C. bescii*. (A) pDCW68 (B) pATHE01 (C) pATHE02 (D) pDCW68 isolated from *E. coli* DH5α incubated with CFE from *C. bescii* (E) pATHE01 and pATHE02 isolated from *C. bescii* incubated with CFE from *C. bescii* (F) pDCW68 isolated from *E. coli* treated with M.HaeIII and incubated with CFE from *C. bescii*. Features originating from *E. coli* are shaded in black and from *C. bescii* are white; $Apr^R$, apramycin resistant gene cassette; Trp, Cbes 2105-trytophan synthetase a subunit; OriT, origin of transfer for conjugation; pSC101, low copy replication origin in *E. coli*; HaeIII restriction sites are indicated. All incubation times were as indicated.

With the reclassification of *A. thermophilum* to *C. bescii*, the nomenclature used to refer to, for example, certain plasmids shown in FIG. 1 also has changed. For example, pATHE01 is now known as pBAL. Similarly, pATHE02 is now known as pBAS2.

As used herein, the following terms shall have the indicated meanings.

"CbeI" refers to a polypeptide encoded by at least a portion of the coding region of Cbes 2438 and that cleaves DNA at a 5'-GG/CC-3'. CbeI can refer to a 38 kDa polypeptide encoded by a 981 bp coding sequence of Cbes 2438, or a biologically active fragment of such a polypeptide. Biological activity, in the context of CbeI, refers to the ability to digest DNA specifically at a 5'-GG/CC-3' recognition site at a temperature from 35° C. to 85° C.

"M.CbeI" refers to a polypeptide encoded by at least a portion of the coding region of Cbes 2437 and that, when incubated with DNA at a temperature from 35° C. to 85° C. methylates a cytosine in the 5'-GG/CC-3' recognition site of CbeI.

"Methylase" and "methyltransferase" are synonymous as used herein and may be used interchangeably.

The term "and/or" means one or all of the listed elements or a combination of any two or more of the listed elements.

The terms "comprises" and variations thereof do not have a limiting meaning where these teens appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

A potent HaeIII-like DNA restriction activity was detected in cell-free extracts of *Caldicellulosiruptor bescii* DSM 6725 using plasmid DNA isolated from *E. coli* as substrate. Incubation of the plasmid DNA in vitro with HaeIII methyltransferase partially protected it from cleavage by HaeIII nuclease as well as cell-free extracts of *C. bescii*. The gene encoding the putative restriction enzyme was cloned and expressed in *E. coli* with a His tag at the C-terminus. The purified protein was 38 kDa as predicted by the 981 bp nucleic acid sequence, was optimally active at temperatures between 75° C. and 85° C. and was stable for more than a week when stored at 35° C. The cleavage sequence was determined to be 5'-GG/CC-3' indicating that CbeI is an isoschizomer of HaeIII. A search of the *C. bescii* genome sequence revealed the presence of both a HaeIII-like restriction endonuclease (Cbes 2438) and DNA methyltransferase (Cbes 2437). Preliminary analysis of other *Caldicellulosiruptor* species suggested that this restriction/modification activity is widespread in this genus. A phylogenetic analysis based on sequence alignment and conserved motif searches identified features of CbeI distinct from other members of this group and classified CbeI as a member of a novel subfamily of HaeIII-like enzymes.

While described below in terms of introducing heterologous polynucleotides into thermophilic and/or hyperthermophilic species, the methods described herein also may be used more generally to introduce polynucleotides—whether heterologous or homologous—into such species in order to, for example, achieve overexpression of the polynucleotide, overproduction of at least one polypeptide encoded by the introduced polynucleotide, and an increase in the cellular level of activity of the encoded polypeptide.

Also, the methods described herein may be used generally to introduce polynucleotides into other thermophilic species such as, for example, certain *Clostridium* spp. and/or hyperthermophilic species such as, for example, *Thermoanaerobacter* spp.

The ability to genetically manipulate *Caldicellulosiruptor* species—and other thermophilic or hyperthermophilic species—is a prerequisite for their use in consolidated bioprocessing. In our efforts to develop a method of DNA transformation, we discovered several potent restriction activities, one of which we describe in this report. The activity of host restriction enzymes is a major barrier to the introduction of DNA into cells. Identifying and overcoming restriction systems has allowed the development of genetic systems in previously non-transformable bacteria. Often this is accomplished by in vitro methylation or by in vivo methylation systems in, for example, *E. coli*. For example, in the thermophile *Bacillus methanolicus*, plasmids are engineered with fewer BmeI recognition sites and prepared in a dam$^+$ *E. coli* strain in order for transformation to occur (Cue et al., 1997 Appl Environ Microbiol 63:1406-1420). In *Prevotella* species and *Helicobacter pylori*, plasmid DNA is methylated by cell-free extracts to achieve transformation by electroporation (Accetto et al., 2005 FEMS Microbiol Left 247:177-183; Donahue et al., 2000 Mol Microbiol 37:1066-1074). In *Clostridium difficile*, plasmids are constructed that lack CdiI and Sau96I recognition sequences (Purdy et al., 2002 Mol Microbiol 46:439-452). *Clostridium perfringens* type B transformation can occur only when the transforming plasmid DNA is isolated from a dam$^+$dcm$^+$ strain of *E. coli* (Chen et al., 1996 FEMS Microbiol Lett 140:185-191). *Clostridium cellulolyticum* can be transformed only if the plasmid DNA is protected from CceI cleavage using either in vitro or in vivo methylation (Jennert et al., 2000 Microbiology 146(Pt12): 3071-3080).

In our efforts to develop efficient methods for DNA transformation of *C. bescii*, we identified a potent thermostable Type II restriction endonuclease that is an isoschizomer of HaeIII (Middleton et al., 1972 J Virol 10:42-50). HaeIII-like enzymes are a diverse group of proteins with distinct catalytic domains that have in common the ability to cleave the same DNA sequence. The prototype of this group, HaeIII, was first identified in *Haemophilus aegyptius* in 1972 (Middleton et al., 1972 J Virol 10:42-50). This enzyme recognizes 5'-GGCC-3' and cleaves the DNA between the second G (in the second position) and first C (in the third position) leaving a blunt end. HaeIII-like restriction activity is widespread in bacteria and archaea (Roberts et al., 2010 Nucleic Acids Res 38:D234-D236) allowing efficient restriction of foreign DNA. Four-base cutters like HaeIII can present a challenge for DNA transfer since the expected frequency of the cleavage sites sequence is greater than the expected frequency of longer recognition sequences. The enzyme identified from *C. bescii* was named CbeI and its cleavage activity, temperature profile, and thermostability are described.

This is the first investigation of a restriction-modification system in any species of *Caldicellulosiruptor*. Bioinformatic analysis of CbeI and other HaeIII isoschizomers reveals a previously unidentified subfamily of this group of restriction endonucleases. The work described herein advances the study of the nature of restriction-modification systems and advances efforts to establish genetic methods for this important group of organisms.

Identification of a HaeIII-Like Restriction Activity in *C. bescii*.

A cell-free extract from *C. bescii* was prepared (Jennert et al., 2000 Microbiology 146(Pt12):3071-3080) and incubated with pDCW68 DNA (FIG. 1A), a vector constructed for use in transformation experiments and that had been isolated from *E. coli* (DH5α dam⁺dcm⁺). The plasmid DNA, when incubated with the *C. bescii* cell-free extract, was completely digested within 10 minutes and had a similar restriction cleavage profile to that of a digest with commercially available HaeIII (FIG. 1D). DNA of the two native *C. bescii* plasmids, pATHE01 and pATHE02 (FIGS. 1B and 1C), were not digested when incubated with the same cell-free extract nor were they digested by commercially available HaeIII endonuclease (FIG. 1E) suggesting the presence of HaeIII methyltransferase-like activity in *C. bescii*. In addition, pDCW68 DNA that had been methylated in vitro by commercially available HaeIII methyltransferase was protected from cleavage from either the commercially available HaeIII restriction enzyme or cell-free extracts from *C. bescii* (FIG. 1F), suggesting the presence of a cognate methyltransferase activity in *C. bescii*. In support of the notion that *C. bescii* contains a HaeIII-like enzyme is the observation that HaeIII recognition sites (GGCC) are much less abundant in the *C. bescii* genome sequence than would be expected based on random nucleotide composition (0.468 observed/expected). Organisms that produce restriction enzymes often have a bias against the presence of the recognition sequences of those enzymes in their genomes (Nobusato et al., 2000 Gene 259:89-98; Rocha et al., 2001 Genome Res 11:946-958). We have named this HaeIII-like restriction endonuclease from *C. bescii*, CbeI. Cloning, Expression, and Purification of CbeI from *Caldicellulosiruptor bescii*.

A query of the *C. bescii* genome using the GenBank (Benson et al., 2009 Nucleic Acids Res 37:D26-31) database as well as REBASE (Roberts et al., 2010 Nucleic Acids Res 38:D234-D236) identified a methyltransferase (Cbes 2437) adjacent to a candidate gene for a HaeIII-like restriction endonuclease (Cbes 2438) (FIG. 2A), which is a common feature of Type II restriction/modification gene arrangements (Kong et al., 2000 Nucleic Acids Res 28:3216-3223).

The open reading frame encoding CbeI (Cbes 2438) was cloned into an *E. coli* expression vector, pDCW72 (FIG. 2B) under the transcriptional control of the T7 promoter to allow regulated expression of the restriction endonuclease as it would be expected to be toxic to cells that did not contain the corresponding methyltransferase. In fact, initial attempts to clone the gene encoding a His-tagged version, CbeI-His$_6$, at 37° C., even without induction of the T7 promoter, failed. Because *C. bescii* grows optimally near 80° C., we investigated the possibility that the cloning and expression of CbeI at lower temperatures would be more efficient because at lower temperatures the enzyme might be inactive or non-functional. When experiments were done at 23° C. (the equivalent of expressing *E. coli* enzymes at −6° C.) both cloning and expression were successful. Since there are also significant differences in codon usage between *C. bescii* (35.2% GC content) and *E. coli* (50.5% GC content), BL21-CodonPlus(DE3)-RIPL cells which contain rare tRNAs were used for expression. Preparations of purified C-terminal His-tagged CbeI contained a single band on an SDS-PAGE gel (FIG. 2C) with a molecular mass of approximately 38 kDa which is consistent with the calculated value of 37.9 kDa determined using the Compute pI/Mw analysis tool.
Functional Analysis and Temperature Optimum of the Purified CbeI endonuclease Activity.

A DNA substrate containing three HaeIII restriction sites (FIG. 3A), which should generate fragments of 1393 bp, 772 bp, 293 bp, and 106 bp when digested, was used in restriction digestion assays. Purified CbeI protein (12-48 ng) was incubated with 50 mM potassium acetate, 20 mM Tris-acetate, 10 mM magnesium acetate, 1 mM dithiothreitol at pH 7.9, and 100 ng of DNA substrate in 10 µl (FIG. 3A), and incubated for 10-20 minutes at 75° C. These conditions were chosen based on the reaction conditions of other isoschizomers of HaeIII from thermophiles (Nö ing and de Vos, 1992 J Bacteriol 174:5719-5726; Prangishvili et al., 1985 FEBS Lett 192:57-60) and on the composition of NEB Buffer 4 that is used with commercially available HaeIII restriction endonuclease.

Experiments with cell free extracts indicated that CbeI cleavage activity occurred within 10 minutes even with low protein concentrations (4 µg total cell protein in 60 µl). Purified protein showed a similar time course and there was no difference in activity between 12 ng to 48 ng (in 10 µl) of purified protein in the enzyme assays. The experiment shown in FIG. 3B used 24 ng (in 10 µl) of purified protein. In assays with less than 2.5 ng (in 10 µl) of protein, no activity was detected.

Figure 3:
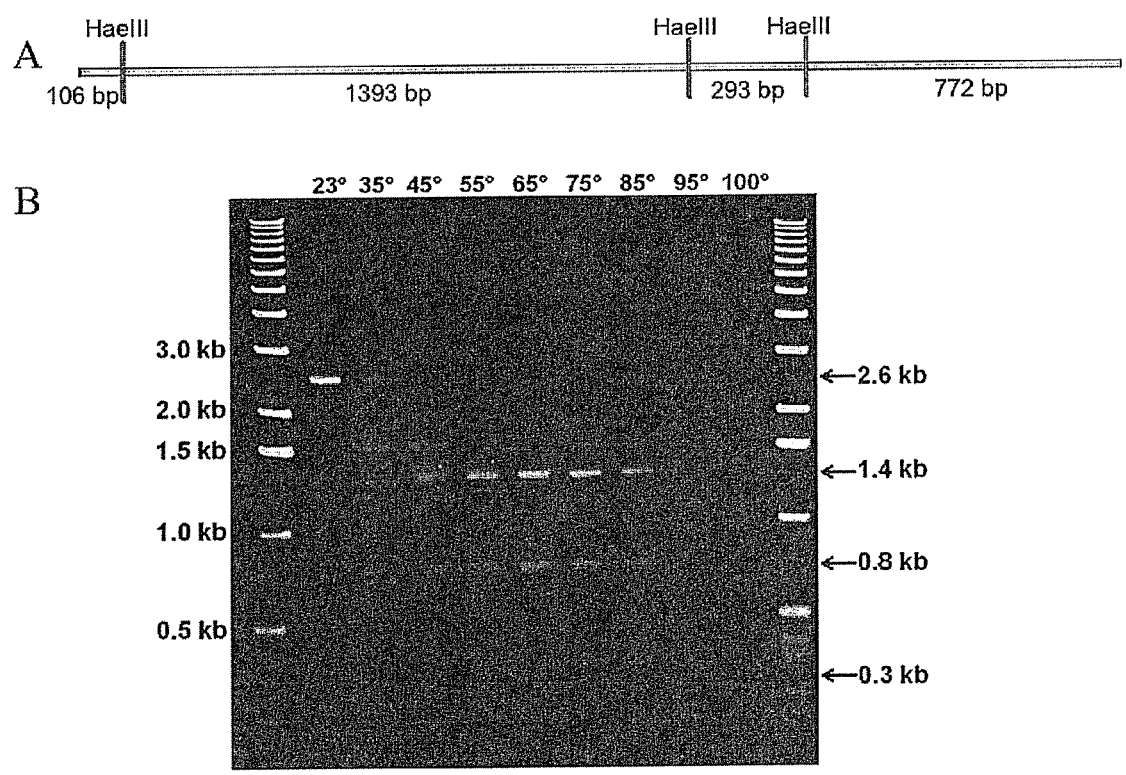
FIG. 3. Temperature profile of purified CbeI endonuclease activity. (A) The 2.558 kb DNA substrate synthesized as described in the Materials and Methods. HaeIII cleavage sites are marked by vertical lines and predicted cleavage fragment sizes are indicated below the line. (B) pDCW72 used to his-tagged expression of CbeI. The substrate was incubated for 10 minutes with 5 ng of protein at the temperatures indicated and the cleavage products were separated on 1.2% agarose gel. The position of the full length undigested fragment and the three major cleavage products derived by digestion with CbeI are indicated by arrows.

During the course of cloning and expressing CbeI in *E. coli*, the gene was not toxic to cells grown at 23° C. but it was at 37° C., suggesting that the enzyme was less active at low temperature. To determine the optimal temperature for CbeI activity, purified protein was incubated with the DNA substrate at temperatures ranging from 23° C.-100° C. As shown in FIG. 3B, the enzyme is optimally active between 75° C. and 85° C., exhibiting partial digestion activity at 45° C. or below and non-specific activity above 85° C. No activity was detected at 23° C. The optimum temperature for commercially available HaeIII activity is 37° C. and the enzyme is inactivated by treatment at 80° C. for 20 minutes. In contrast, CbeI is optimally active at 75° C.-85° C. and is stable for more than 30 minutes at 75° C. (FIG. 3B). CbeI did not lose activity after storage for more than one week stored at up to 35° C. and was heat-inactivated by incubation at 100° C. for 5 minutes.
CbeI is an Isoschizomer of HaeIII.

HaeIII recognizes a sequence that includes GGCC and cleaves between the G and C leaving a blunt ended fragment. To determine the cleavage site of CbeI, a DNA fragment containing three HaeIII recognition/cleavage sites (FIG. 3A) was used as substrate with purified CbeI enzyme. The cleavage products were either ligated directly to pWSK29 that had been digested with EcoRV leaving a blunt end, or first treated with the Klenow fragment of DNA polymerase prior to ligation. The sequence of the region containing the cloning site revealed the dinucleotide 5'-CC-3' adjacent to the EcoRV site and the dinucleotide 5'-GG-3' adjacent to the EcoRV site, identifying 5'-GG/CC-3' as the CbeI cleavage site. The same result was obtained in eight independent cloning experiments, indicating that CbeI is an isoschizomer of HaeIII.
Cluster Analysis of HaeIII-Like Proteins Reveals that CbeI is a Member of a New Subfamily of HaeIII-Like Enzymes.

Figure 4:
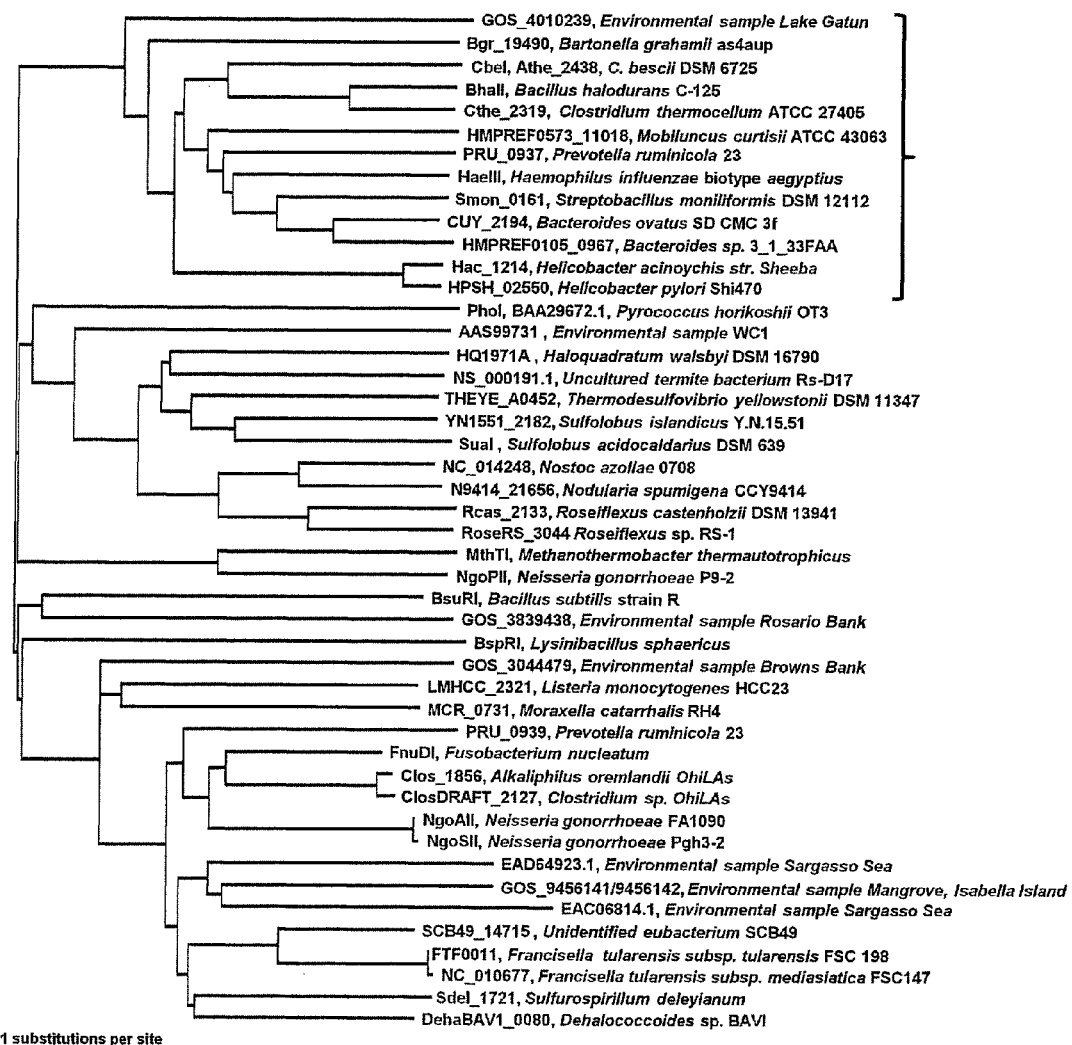
FIG. 4. Phylogram alignment of 46 HaeIII-like restriction enzymes. The host organism for each restriction enzyme is indicated as well as the protein name, when available. Otherwise, the GenBank locus tag or accession number is given. The distance scale is indicated by a bar defining the distance for 0.1 amino acid substitution per site. The bracketed organisms represent those containing this new subfamily of HaeIII-like enzymes that includes CbeI.
Figure 5:
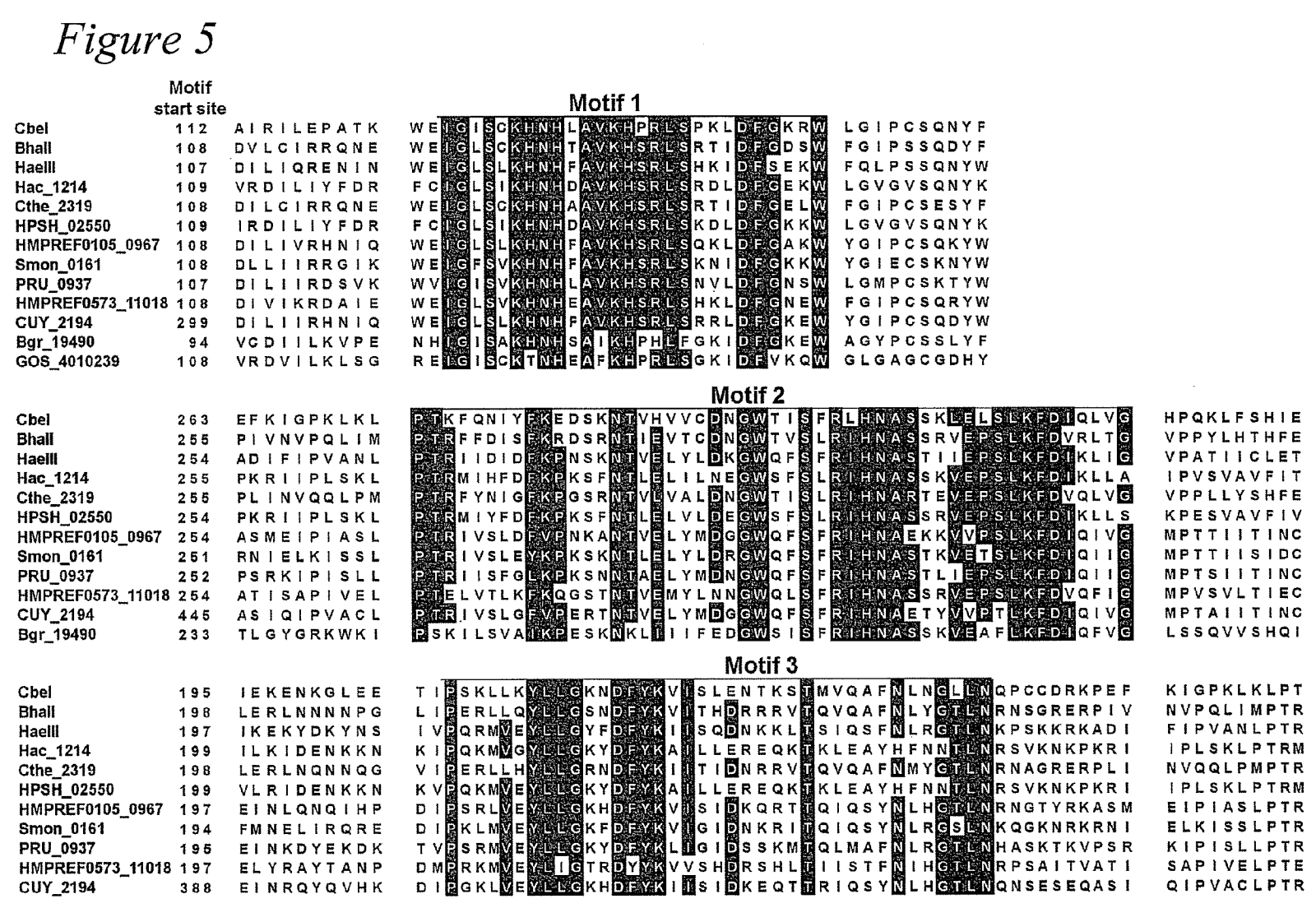

A search of the REBASE and NCBI databases revealed 231 HaeIII-like proteins. Of those, 183 had been fully or partially characterized and 48 were putative isoschizomers predicted from their DNA sequences. Of the 57 proteins for which there were sequence information available, subfamilies of the same genus and species were removed leaving 46 sequences used in this analysis. A phylogram based on protein sequence alignments is shown in FIG. 4. CbeI falls into a distinct group of 13 proteins, five of which had previously been grouped (pfam09556) based on overall sequence similarity using the Conserved Domain Database (Marchler-Bauer et al., 2009 Nucleic Acids Res 37:D205-210). Our own motif-based sequence analysis (MEME Suite and GLAM2) of this group of 13 proteins with other HaeIII-like proteins identified three conserved motifs shared by 11 of the 13 (FIG. 5), but not present in other HaeIII-like proteins. One protein (Bgr_19490) had motifs 1 and 2, and one (GOS_4010239) had only motif 1.

Evidence for HaeIII-Like Restriction/Modifications Systems in Other *Caldicellulosiruptor* Species.

Figure 6:
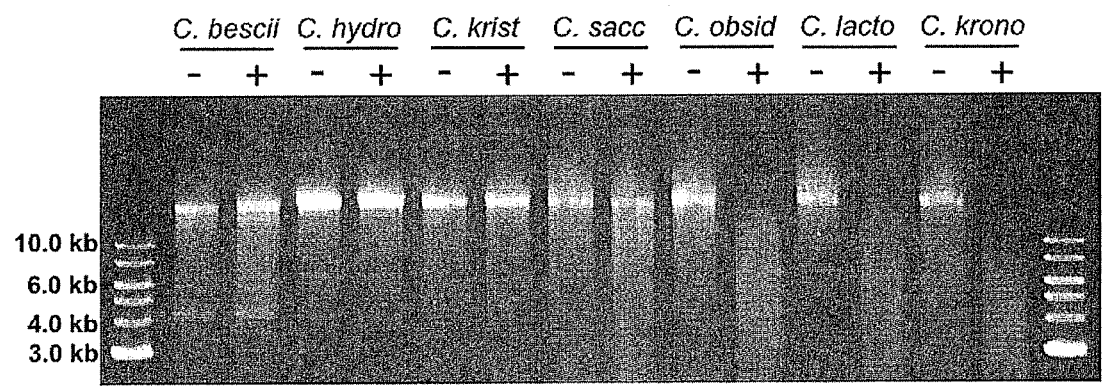
FIG. 6. Distribution of HaeIII-like restriction/modification systems in *Caldicellulosiruptor* species. Total DNA isolated from 7 different species were incubated (−) without or (+) with commercially available HaeIII endonuclease at 37° C. for 1 hour according to the manufacturer's instructions (NEB). *C. bescii; C. hydro, C. hydrothermalis; C. krist, C. krisyansonii; C. sacc, C. saccharolyticus; C. obsid, C. obsidiansis; C. lacto, C. lactoaceticus; C. krono, C. kronotskyensis*. Also visible in the *C. bescii* lanes are the undigested native plasmids from that strain, pATHE01 (8.3 kb) and pATHE02 (3.6 kb).

To investigate whether other *Caldicellulosiruptor* species contained HaeIII-like restriction/modification activities, total DNA was isolated from a number of *Caldicellulosiruptor* species and incubated with commercially available HaeIII restriction endonuclease. As shown in FIG. 6, *C. saccharolyticus* DSM 8903, *C. hydrothermalis* DSM 18901, *C. kristjanssonii* DSM 12137, and *C. bescii* DSM 6925 were resistant to HaeIII nuclease while *C. kronotskyensis* DSM 18902, *C. lactoaceticus* DSM 9545, *C. obsidiansis* ATCC BAA-2073, were sensitive. These preliminary data suggest that this HaeIII-like restriction/modification system may be widespread among members of this genus.

Identification of M.CbeI

Figure 2:
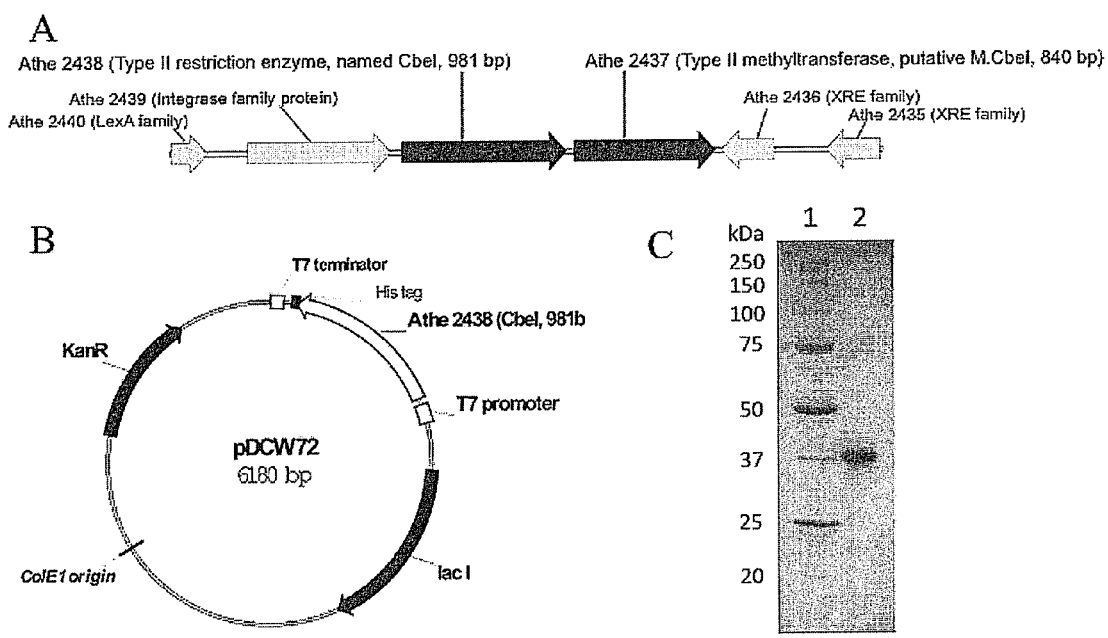
FIG. 2. Cloning, expression and purification of CbeI. (A) The region surrounding the location of CbeI in the *C. bescii* genome. (B) pDCW72; KanR, kanamycin resistance gene; bacteriophage T7 promoter and T7 terminator; IacI, the gene for the lactose repressor protein; ColEI, origin of replication derived from pBR322 (C) Lane 1: protein molecular weight standards; lane 2: 15 ng of purified CbeI protein displayed on a 10-20% Tris-HCl gradient gel (CRITERION Precast Gel, Bio-Rad Laboratories; Hercules, Calif.).

As described above, CbeI from *C. bescii* DSM 6725 is an isoschizomer of HaeIII (cuts at the same site) which is a Type II restriction enzyme. Type II restriction enzymes and their cognate methyltransferase genes are often adjacent to each other in the chromosome. The locations of the coding region for CbeI (Cbes 2438) and the coding region for the cognate methyltransferase (Cbes 2437) are indicated in FIG. 2A.

Figure 7:
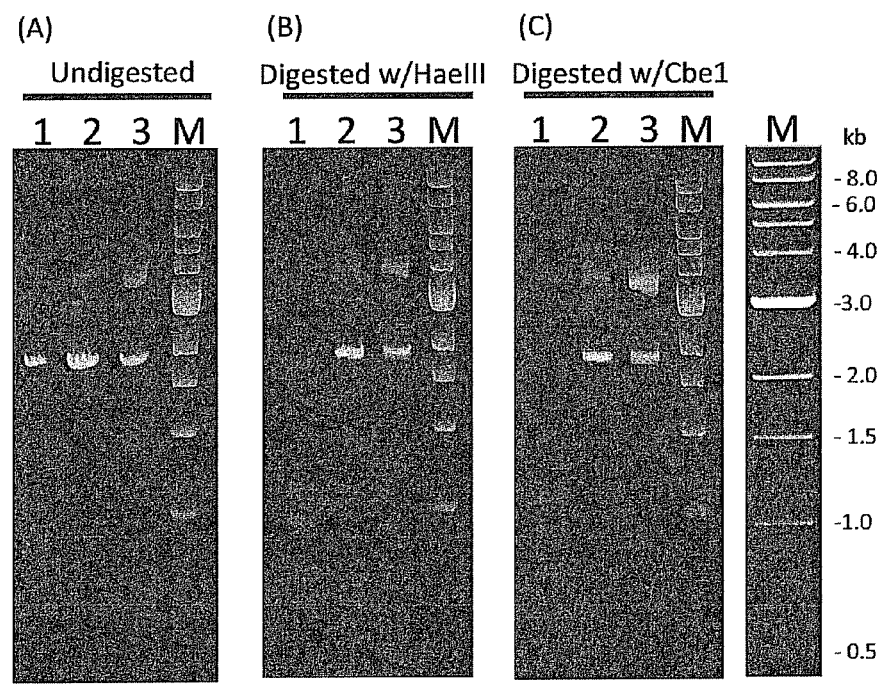
FIG. 7. Plasmid DNA (pUC18) was isolated from *E. coli* and incubated in vitro with either M.HaeIII methyltransferase (NEB) or M.CbeI methyltransferase. After digestion with either HaeIII or CbeI (as indicated) fragments were displayed on a 1.2% TAE-agarose gel stained with ethidium bromide. Lanes 1) un-methylated pUC18 DNA; 2) pUC18 treated with M.HaeIII; 3) pUC18 treated with M.CbeI are as indicated in each panel; Panel (A) no restriction enzyme added (B) with HaeIII for 30 minutes at 37° C. or (C) with CbeI for 30 minutes at 75° C. MW: 1 kb DNA ladder (NEB).
Figure 8:
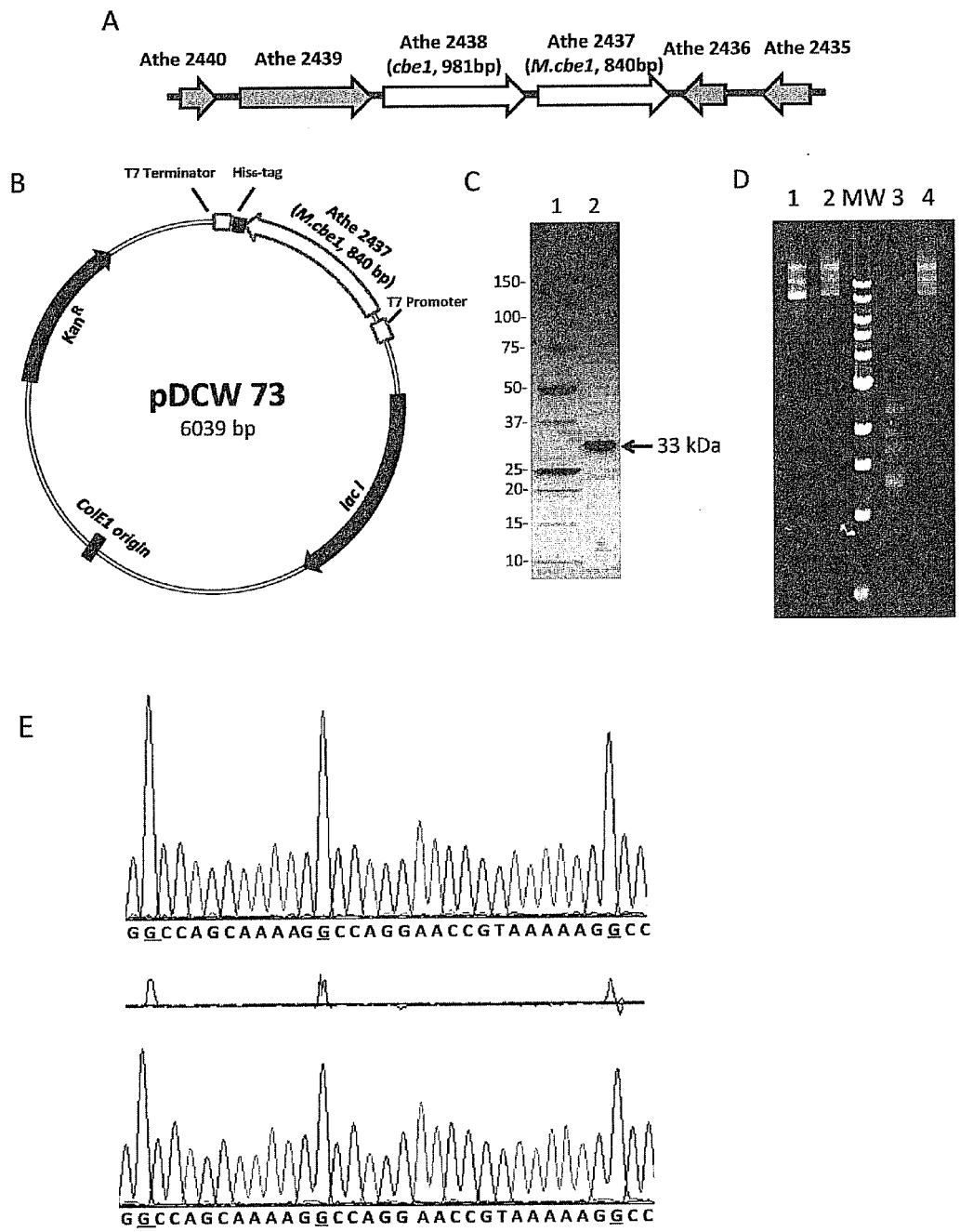
FIG. 8. Expression, purification, and characterization of M.CbeI. (A) Physical map of surrounding region of M.CbeI in the *C. bescii* genome. (B) Schematic diagram of pDCW73; KanR, kanamycin resistance gene; bacteriophage T7 promoter and T7 terminator; lacI, the gene for the lactose repressor protein; ColEI, origin of replication derived from pBR322 (C) Coomassie blue stained SDS-PAGE gel. Lane 1: protein molecular weight standards; lane 2: 15 ng of purified M.CbeI protein displayed on a 10-20% Tris-HCl gradient gel (Criterion™ Precast Gel, Bio-Rad Laboratories, Hercules, Calif.). The molecular weight of the purified His-tagged M.CbeI proteins is indicated by an arrow on the right. (D) M.CbeI methylation sensitivity of CbeI. Lane 1: Undigestged unmethylated pDCW 70; Lane 2: Undigested M.CbeI methylated pDCW 70; Lane 3: Digested with purified CbeI of unmethylated pDCW 70; Lane 4: Digested with purified CbeI of M.CbeI methylated pDCW 70; M: 1 kb DNA ladder (NEB). (E) Differences between G signals to M.HaeIII (top panel; SEQ ID NO:49) and M.CbeI (bottom panel; SEQ ID NO:50) methylated innercytosine residue in 5'-GGCC-3' sequence. Trace differences in G residue between M.HaeIII and M.CbeI methylated pUC18 is shown in middle panel.

The coding region of M.CbeI was cloned and shown in FIG. 8. Plasmid DNA (pUC18) was isolated from *E. coli* and incubated in vitro with either M.HaeIII methyltransferase (NEB) or M.CbeI methyltransferase. FIG. 7 shows the result of those digestions. M.CbeI protected pUC18 DNA from digestion by HaeIII for 30 minutes at 37° C. (middle gel, lane 3) and from digestion by CbeI for 30 Minutes at 75° C. (right panel, lane 3).

Cbes 2437 had been annotated in the GenBank database as a "D12 class N6 adenine-specific DNA methyltransferase," which would indicate that it is not a methyltransferase that would protect DNA from cleavage. Since CbeI cleaves the sequence 5'-GG/CC-3', a cytosine-specific methyltransferase would be necessary in order to protect the chromosomal DNA from CbeI restriction endonuclease activity. Thus, prior to our characterization of the expression product of M.CbeI, the expression product of Cbes 2437, Cbes 2437 was incorrectly identified to lead one away from the possibility that it could encode a cognate methyltransferase that would protect chromosomal DNA from digestion by CbeI.

Two other *Caldicellulosiruptor* species (*C. hydrothermalis* and *C. kristjanssonii*) may contain the same HaeIII-like CbeI/ M.CbeI restriction-modification system—i.e., homologues of CbeI and M.CbeI, suggesting that this may be a wide spread system in *Caldicellulosiruptor* species.

M.CbeI is a novel methyltransferase only present in *Caldicellulosiruptor* species (in *C. hydrothermalis* the gene locus tag is Calhy 0409 and in *C. kristjanssonii* 177R1B the gene locus tag is Calkr 2088). M.CbeI is also distinctly different both in DNA sequence and protein sequence from M.HaeIII and its isoschizomers, the models for 5'-GGCC-3' methylation.

After DNA replication in bacterial cells, methyltransferases can modify DNA in one of three ways to either methylate adenine to $N^6$-methyladenine ($m^6A$), cytosine to $N^4$-methylcytosine ($m^4C$), or cytosine to 5-methylcytosine ($m^5C$). A study of methylation of nucleotide bases in thermophiles with optimal growth temperatures above 60° C. revealed that the presence of $m^4C$ is favored over $m^5C$, since $m^5C$ has a tendency to be deaminated to thymine by heat (e.g., temperatures greater than 70° C.), thereby causing C-T transition mutations. Thus, the CbeI cognate methyltransferase (Cbes 2437) does not methylate cytosine to $m^5C$ as M.HaeIII does, but instead methylates cytosine to the more heat-stable $m^4C$.

M.CbeI is the first example of an α-class (F_G_G-TRD-DPPY) $N^4$-methylcytosine methyltransferase specific for 'GGCC'. This may explain why commercially available 'GGCC' methyltransferase (M.HaeIII) treatment was not successful in protecting the DNA for transformation into *C. bescii*.

Thus, in a screen of *C. bescii* cell-free extracts for restriction endonuclease activities we discovered a potent HaeIII-like restriction activity with novel features. Plasmid DNA from *E. coli*, but not plasmid DNA from *C. bescii*, was digested within 10 minutes of incubation with these extracts and treatment with HaeIII methyltransferase partially protected the DNA from cleavage suggesting the existence of a HaeIII-like restriction-modification system in *C. bescii*. Bioinformatic analysis of the *C. bescii* genome identified a gene encoding a protein homologous to the HaeIII endonuclease and an adjacent gene encoding a Type II DNA methyltransferase. The gene for the endonuclease was cloned and expressed in *E. coli* with a His-tag. Purified enzyme from *E. coli* was optimally active between 55° C. and 85° C. and was stable at 35° C. for more than a week. The cleavage site of the enzyme was determined to be GG/CC suggesting that it is an isoschizomer of HaeIII and we have named this enzyme CbeI. A phylogram of CbeI with other HaeIII-like enzymes identified a new subfamily of these enzymes with unique features.

The cloning and expression of CbeI in *E. coli* presented some challenges, as does the expression of other toxic genes including other restriction endonucleases (Kong et al., 2000 Nucleic Acids Res 28:3216-3223; Rasko et al., 2010 Nucleic Acids Res 38:7155-7166). In addition to using BL21-Codon-Plus(DE3)-RIPL cells to compensate for differences in codon usage between *E. coli* and *C. bescii*, we took advantage of the fact that CbeI is from an extreme thermophile and would be expected to have minimal activity at temperatures significantly below the growth temperature of *C. bescii* ($T_{opt}$~80° C.). This appeared to be the case since expression of CbeI was apparently toxic to *E. coli* cells grown at 37° C., but it was expressed efficiently at 23° C. This strategy may be useful for expressing toxic genes derived from thermophilic organisms in *E. coli*, eliminating the need for complicated highly-regulated expression systems and without the corresponding methyltransferase.

Since the first description of the HaeIII restriction enzyme in 1972 (Middleton et al., 1972 J Viral 10:42-50), more than 200 isoschizomers have been reported or predicted (Roberts et al., 2010 Nucleic Acids Res 38:D234-D236). Of these, fewer than 40 are from thermophiles (organisms that have $T_{opt} \geq 50°$ C.), and only three of these have been characterized: MthTI (Nölling and de Vos, 1992 J Bacteriol 174:5719-5726) from *Methanobacterium thermoformicicum* THF ($T_{opt}$ 55° C.), NspLKI (Zabaznaya et al., 1999 Biochemistry (Mosc) 64:189-193) from *Nocardia* species LK ($T_{opt}$ 50° C.), and SuaI (Prangishvili et al., 1985 FEBS Lett 192:57-60) from *Sulfolobus acidocaldarius* ($T_{opt}$ 82° C.). A fourth, PhoI from *Pyrococcus horikoshii* ($T_{opt}$ 98° C.), is commercially available (New England Biolabs; Ipswich, Mass.) but there are no reports on this enzyme in the literature. Unlike HaeIII itself, which is optimally active at 37° C. and is inactivated by heating to 80° C., CbeI was optimally active in the range 75° C.-85° C. and required incubation at 100° C. for 5 minutes for inactivation. The fact that CbeI isolated from *E. coli* is thermostable suggests that this feature is due to its conformation, hydrophobic, electrostatic, or other properties rather than by association with other proteins or cofactors in *C. bescii*.

HaeIII-like enzymes are widespread in both the archaea and bacteria. Genes encoding NgoPII from *Neisseria gonorrhoeae*, a bacterium, and MthTI from *Methanobacterium*

*thermoformicicum*, an archaeon, have unexpectedly high similarity (54.5% nucleotide identity) suggesting horizontal gene transfer (Milling and de Vos, 1992 J Bacteriol 174:5719-5726). In fact, a phylogenetic tree based on protein sequence similarity of HaeIII-like proteins (FIG. 4) identified a subgroup that includes four proteins from archaea (*Pyrococcus horikoshii* OT3, *Sulfolobus islandicus, Sulfolobus acidocaldarius*, and *Methanothermobacter thermautotrophicum*) and nine from bacteria, suggesting that there may have been cross-domain horizontal gene transfer for these proteins. In support of this notion is the fact that the GC-content of some of the genes encoding HaeIII-like proteins is significantly different from that of their host organism chromosomes: *Mobiluncus curtisii* (55% genome, 46% HMPREF0573), *Prevotella ruminicola* (47% genome, 32% PRU_0939), and *Roseiflexus castenholzii* (60% genome, 52% Rcas_2133). HaeIII-like enzymes are also widespread in both archeael and bacterial thermophiles, such as *Clostridium thermocellum* ATCC 27405, *Methanothermobacter thermautotrophicum* THF (Nölling and de Vos, 1992 J Bacteriol 174:5719-5726), *Nocardia* species LK (Zabaznaya et al., 1999 Biochemistry (Mosc) 64:189-193), *Roseiflexus castenholzii* DSM 13941, *Sulfolobus islandicus, Sulfolobus acidocaldarius* DSM 639 (Prangishvili et al., 1985 FEBS Lett 192:57-60), *Pyrococcus horikoshii* OT3, and *Thermodesulfovibrio yellowstonii* DSM 11347.

In an analysis of 46 HaeIII-like proteins, those most similar to CbeI were found in other bacteria, both Gram-positive and Gram-negative. CbeI exhibits the highest amino acid sequence similarity (~60%) with the HaeIII-like proteins from *Bacillus halodurans* (BhaII) and *Clostridium thermocellum* (Cthe_2319). Examination of genomic DNA isolated from seven different *Caldicellulosiruptor* species showed that four of the seven were resistant to HaeIII cleavage indicating that HaeIII-like restriction-modification systems may be widespread in members of this genus (FIG. 6).

An amino acid sequence alignment of CbeI and the 12 closely-related HaeIII-like proteins (bracketed in FIG. 4) revealed highly conserved residues that define three previously unrecognized motifs that may play a role in their structure or catalytic. Although these thirteen HaeIII-like proteins could not be reliably matched to any other known protein structure or to the five known type II restriction endonuclease superfamilies (PD-(D/E)XK, HNH, PLD, GIY_YIG, and HALFPIPE) (Orlowski and Bujnicki, 2008 Nucleic Acids Res 36:3552-3569), these observations make CbeI an interesting candidate for structural analyses since it may possess a novel tertiary structure. This new subgroup identified in our analysis that includes CbeI defines a new subfamily of structurally or functionally related proteins in this diverse group of enzymes. The results presented here also have important implications in the development of methods of genetic transformation for this interesting and biotechnologically-important group of relatively uncharacterized organisms.

Type II restriction endonucleases like CbeI can be a barrier to DNA transformation of several bacterial strains. Thus, successful transformation of such bacterial strains can involve overcoming restriction by the hosts. Approaches include engineering the transforming DNA to contain fewer restriction sites (Gallagher et al., 2008 J Bacteriol. 190(23): 7830-7; Cue et al., 1997 Appl Environ Microbiol. 63(4): 1406-20; Purdy et al., 2002 Mol Microbiol. 46(2):439-52), in vitro methylation by purified methyltransferases (Jennert et al., 2000 Microbiology 146(Pt12):3071-80) or cell extracts (Accetto et al., 2005 FEMS Microbiol Lett. 247(2):177-83; Donahue et al., 2000 Mol Microbiol. 37(5):1066-74), or in vivo methylation by *E. coli* (Cue et al., 1997 Appl Environ Microbiol. 63(4):1406-20; Chen et al., 1996 FEMS Microbiol Lett. 140(2-3):185-91). We were unable to transform *C. bescii* in many attempts using a variety of transformation procedures.

Plasmid DNA treated with purified M.HaeIII, in vitro, was partially protected from cleavage by both HaeIII and CbeI in vitro (FIG. 7), but no transformants were detected when this DNA was used in electroporation experiments or added to cells that had been subjected to a procedure to induce natural competence of *C. bescii*. In addition, various strains of *E. coli* containing combinations of methyltransferases that facilitated transformation of the thermophiles *Bacillus methanolicus* and *Clostridium thermocellum* were used to prepare DNA from *E. coli* for transformation but no *C. bescii* transformants were detected using DNA from these strains (Table 2). A gene for an apparent cognate methyltransferase, M.CbeI (Cbes 2437) is present adjacent to CbeI in the *C. bescii* genome as well as the genomes of *C. hydrothermalis* 108 (Calhy 0409) and *C. krisyanssonii* 177R1B (Calks 2088). Cytosine methyltransferases methylate cytosine to either 5-methylcytosine ($m^5C$), as for M.HaeIII, or more rarely to N4-methylcytosine ($m^4C$). Methylation to $m^4C$ may be more common than methylation to $m^5C$, perhaps because $m^5C$ may be more readily deaminated to thymine by heat.

Here we show that restriction can be a barrier to transformation of *Caldicellulosiruptor* by DNA from *E. coli* and that methylation of a novel αclass Type II cytosine methyltransferase can overcome this barrier. While the apparent transformation frequency may be low, the combined frequencies of transformation and recombination allow maker replacement of chromosomal genes with non-replicating vectors providing an essential tool to generate deletions, gene substitutions, His-tags for protein purification and expression of heterologous proteins to identify genes important for biomass utilization as well as extend substrate utilization and biomass conversion in these organisms.

A Spontaneous Deletion of the *C. bescii* pyrBCF Locus Allows Nutritional Selection of Transformants Attempts to use a thermostable kanamycin resistance gene previously used for selection of transformants in *Thermoanaerobacteria* species at 60° C. to select transformants in *C. bescii* was complicated by the fact that *C. bescii*, which that grows optimally at 75° C., grows very poorly at or below 70° C. In fact, growth at 60° C. increased the spontaneous mutation frequency significantly, from $10^{-7}$ to $10^{-5}$, making the detection of transformants over this background of spontaneous drug resistance problematic. Attempts to use a hygromycin phosphotransferase (hph) gene from *E. coli* that had been selected for function at 85° C. in *Sulfolobus solfataricus* were compromised by the level of natural resistance to hygromycin in *C. bescii*. To generate a mutant strain for nutritional selection of transformants, *C. bescii* cells were plated on 5-fluoroorotic acid (5-FOA). OMP decarboxylase, encoded by the pyrF gene in bacteria (ura3 in yeast), converts the pyrimidine analog 5-fluoroorotic acid (5-FOA) to 5-fluorouridine monophosphate which is ultimately converted to fluorodeoxyuridine by the uracil biosynthetic pathway, a toxic product that kills growing cells that are synthesizing uracil. Mutants of pyrF are, therefore, uracil auxotrophs resistant to 5-FOA. Spontaneous resistance to 5-FOA (8 mM) was observed at a frequency of approximately $10^{-5}$ at 60° C. One such mutant contained a deletion the included part of the carboxy terminus of the pyrF (Cbes1377) open reading frame, the entire pyrC (Cbes1376) open reading frame and the amino terminus of pyrB (Cbes1375) open reading frame diagrammed in FIG. 9A, and was used for further analysis.

The extent of the deletion was defined by PCR amplification of the pyrBCF region in the mutant (FIG. 9C) and subsequent sequencing of the PCR product. Since mutations in pyrE also lead to uracil auxotrophy and 5FOA resistance, the region around the pyrE locus was amplified from this strain and sequenced to ensure that it was wild type. While the deletion would be expected to affect only the pyrBCF genes, qPCR analysis was performed to monitor expression of the pyrA gene as well as the Cbes1374 open reading frame predicted to encode a uracil xanthine permease. Expression of pyrA and Cbes 1374 in the deletion mutant was indistinguishable from the wild type, suggesting that the deletion within the pyrBCF locus did not affect expression of surrounding genes.

The ΔpyrBCF strain was a tight uracil auxotroph and because it contained a deletion, reversion to uracil prototrophy was not a concern making prototrophic selection possible no matter how low the frequency of transformation. Growth of this mutant supplemented with uracil (20 µM) was indistinguishable from that of the wild type, reaching a cell density of $1.5 \times 10^8$ in 20 hours. To assay transformation, a non-replicating plasmid was constructed with the wild type copy of the pyrBCF locus but containing an engineered restriction site within the cassette to distinguish it from the chromosomal wild type allele. This plasmid was used to transform the pyrBCF deletion strain selecting marker replacement events that repaired the deletion (strategy diagrammed in FIG. 9A).

We were unable to transform *C. bescii* in many attempts using this strategy with DNA isolated from *E. coli*. We used and modified methods known to work well for other Gram-positive bacteria including electroporation, artificially induced competence, natural competence, and methods that altered membrane permeability. Mating with *E. coli*, a method of DNA transfer that works well for similar bacteria, did not work for *C. bescii* or the other *Caldicellulosiruptor* species we tested using the same approach.

in vivo and/or in vitro Methylation of DNA from *E. coli* Partially Protects DNA from Cleavage but does not Allow Transformation of *C. bescii*

CbeI, a potent restriction endonuclease in *C. bescii*, recognizes and cleaves the same sequence as HaeIII, unmethylated DNA at the sequence 5'-GG/CC-3'. Plasmid DNA treated with purified M.HaeIII in vitro was partially protected from cleavage by both HaeIII and CbeI in vitro (FIG. 7), but no transformants were obtained when this DNA was used in electroporation experiments or added to cells that had been subjected to a procedure to induce natural competence in *Mycobacterium* and *Thermoanaerobaterium* species. In addition, various strains of *E. coli* containing combinations of methyltranferases were used to prepare DNA for transformation (Table 3, below in Example 3), a method that was successful for transforming *Clostridium thermocellum* using a dam$^+$dcm$^-$ *E. coli* strain (Lynd and Guss, personal communication). No transformants of *C. bescii* were detected using DNA from these strains. In total we performed more than 1000 electroporation experiments varying conditions for cell growth, transformation conditions, and assay conditions as well as using DNA from different strains of *E. coli*.

M.CbeI is a Novel α-Class N4-Cytosine Methyltransferase

As shown in FIG. 8A, the region of the chromosome that contains CbeI also contains an open reading frame, Cbes 2437, predicted to encode an adenine specific methyltransferase. This open reading frame was cloned into an *E. coli* expression vector, pDCW73 (FIG. 8B) that placed a His-tag at the carboxy terminus of the protein allowing purification on a Ni-NTA column. *E. coli* cells containing this plasmid were viable at 23° C. but not 37° C. suggesting that expression of M.CbeI was toxic to growing cells. Expression of this methyltransferase was, therefore, performed at 23° C. to avoid problems related to toxicity and in *E. coli* BL21-CodonPlus (DE3)-RIPL to alleviate problems arising from the significant differences in codon usage between M.CbeI and *E. coli* proteins. Purified M.CbeI from *E. coli* was the size predicted from the open reading frame, 33 kDa (FIG. 8C). No cleavage of DNA was detected by purified CbeI at 75° C. when DNA from *E. coli* was methylated in vitro by the purified methyltransferase (FIG. 8D) and we named this enzyme M.CbeI. To determine the optimal temperature for M.CbeI methyltransferase activity, we performed the in vitro methylation reactions with purified M.CbeI at temperatures ranging from 25° C. to 100° C. and tested the modified DNA for restriction by CbeI. Reactions performed between 65° C. and 85° C., the growth temperature range of *C. bescii*, resulted in the best protection against cleavage by CbeI.

Even though CbeI is an isoschizomer of HaeIII and M.CbeI would be expected to methylate the same sequence as M.HaeIII, methyltransferase vary in the sites of methylation and specific or cognate methylation may be required for full protection. The pattern of DNA methylation by M.CbeI was compared to that by M.HaeIII using a method (Rao and Buckler-White, 1998 Nucleic Acids Res 26(10):2505-7; Bart et al., 2005 Nucleic Acids Res 33(14):e124) that relies on the fact that the extent of incorporation of fluorescently labeled dideoxynucleotides during DNA sequencing is influenced by methylated bases in the template DNA. pUC18 DNA was methylated in vitro by either M.CbeI or M.HaeIII and direct sequencing of the DNA revealed that DNA methylated with M.CbeI showed a higher degree of incorporation of dideoxyguanosine in the 5'-GGCC-3' recognition sequence than DNA methylated with M.HaeIII. N4-methylcytosine results in an increase in the complementary G (GGCC) signal and this signature (FIG. 8E) indicates that M.CbeI methylated DNA contains N4-methylcytosine (m$^4$C). M.HaeIII methylates the C5 position of cytosine (m$^5$C).

Methylation of *E. coli* DNA, In vitro, with Purified M.CbeI Protein Allows Transformation of *C. bescii*

Figure 9:
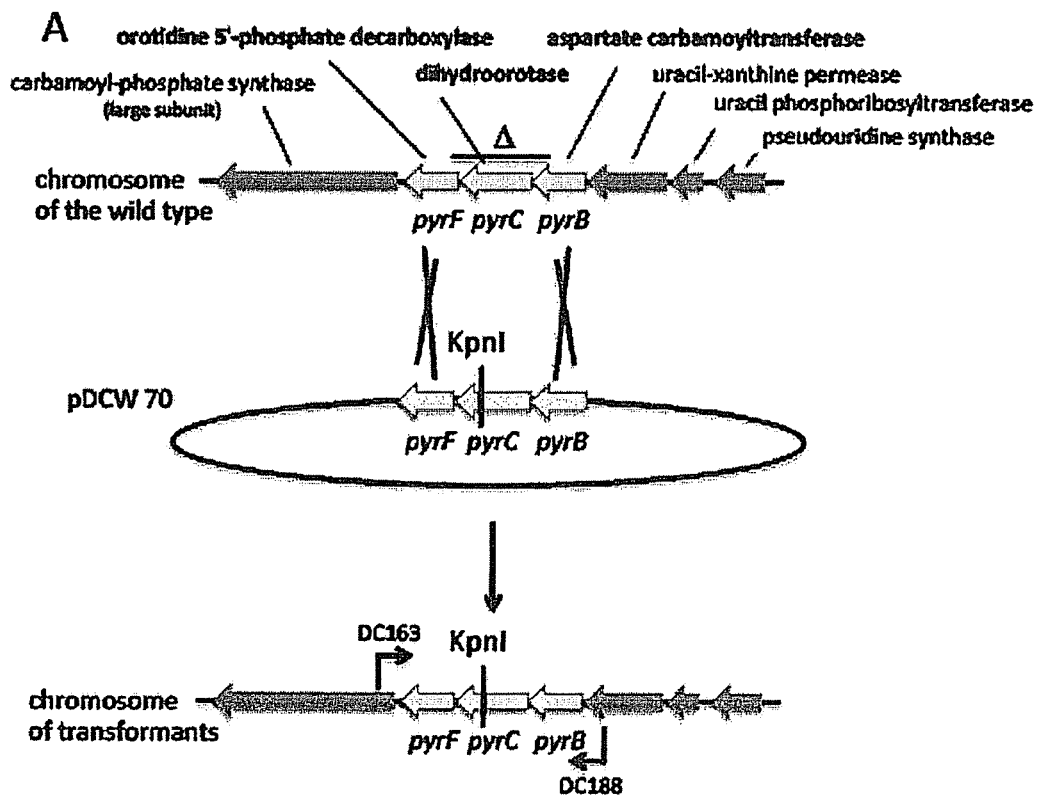
FIG. 9. Confirmation of transformation and marker replacement in ΔpyrBCF strain. (A) A schematic diagrams of the pyrBCF locus wild type (Ura$^+$/5FOA$^S$), ΔpyrBCF (Ura$^-$/5FOA$^R$), pDCW 70, and pyrBCF locus in result transfounant. pDCW 70 having 0.892 kb region of pyrF and 0.662 kb region of pyrB for homologous recombination. Marker replacement by homologous recombination can occur in the chromosome in the pyrBCF region. Engineered KpnI site is indicated, and bent arrows depict primers used for verification of transformation. (B) Electrphoration performance of ΔpyrBCF strain with unmethylated and M.CbeI methylated pDCW 70. Top plate (Defined+Uracil plates), competent cell after electro pulsing; Middle plate (w/o Uracil plate), transformed with unmethylated pDCW 70; Bottom plate (w/o Uracil plate), transformed with M.CbeI methylated pDCW 70. (C) Gel depicting PCR products (amplified by DC163 and DC188), and its cleavage products by KpnI (M: 1 kb DNA Ladder (NEB); Lane 1: Wild type, 3.2 kb; Lane 2: ΔpyrBCF, 1.63 kb; Lane 3: Transformat, 3.2 kb; Lane 4: Wild type cleaved by KpnI, No cleavage; Lane 5: ΔpyrBCF cleaved by KpnI, No cleavage; Lane 6: Transformant cleaved by KpnI, 1.9 and 1.3 kb cleavage products by KpnI).
Figure 9:
Figure 9:
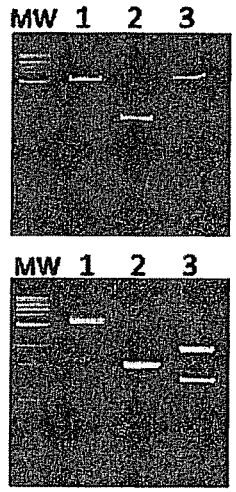

Plasmid DNA from *E. coli* (dam$^+$dcm$^+$) methylated by M.CbeI in vitro readily transformed the *C. bescii* ΔpyrBCF strain resulting in marker replacement of the deletion with the wild type allele containing the engineered KpnI site (FIG. 9C). Amplification of the pyrBCF region from wild type *C. bescii* resulted in a 3.2 kb product while the product generated from the deletion strain was 1.63 kb. Amplification of this region in the transformant generated a wild type size product. Digestion with KpnI resulted in no cleavage of the product generated from the wild type or the ΔpyrBCF mutant. The product generated from transformant was digested with KpnI showing that the transformant contained the allele from the plasmid and its presence in the *C. bescii* chromosome resulted from marker replacement (FIG. 9C). Transformation efficiencies were routinely on the order of 50 transformants per microgram of non-replicating plasmid DNA (Table 3, FIG. 9B). This extremely low transformation efficiency may be an underestimate of the actual efficiency as the plating efficiency of *C. bescii* on selective solid medium is less than $10^{-4}$ (plating $10^6$ cells as determined by cell count resulted in fewer than 100 colonies).

While there are many challenges in the development of transformation protocols, restriction of DNA from *E. coli* by host bacteria is often an issue. Restriction/modification of DNA, first recognized as a mechanism of protection against phage infection, varies in effectiveness depending on the activity of restriction endonuclease and the methylation state of the DNA substrate. Methylation of DNA may either facilitate or limit the activity of endonucleases and plays a major role in transformation of heterologous DNA no matter what the source of the DNA or the host for transformation. Transformation of DNA from *E. coli* to *Caldicellulosiruptor bescii* is apparently especially sensitive to restriction/modification and here we show that the use of a novel endogenous methyltransferase provided specific modification of DNA from *E. coli* that allowed efficient transformation.

Figure 10:
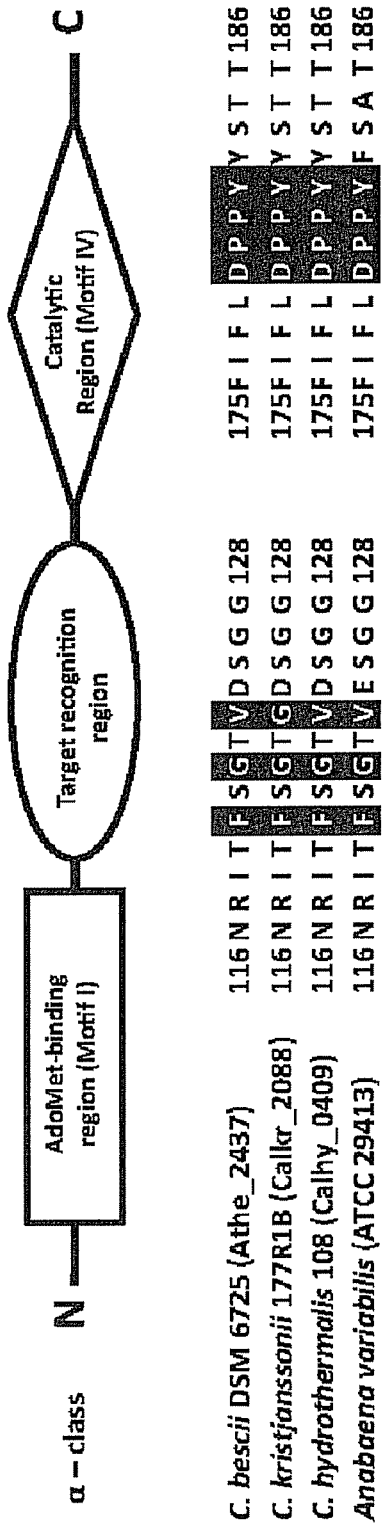
FIG. 10. Linear order of the three functional groups of M.CbeI. Sequence alignment of three members of *Caldicellulosiruptor* species and DmtB from *Anabaena variabilis*, which contain a M.CbeI homologue. Sequences are shown for *C. bescii* DSM 6725 (SEQ ID NO:51); *C. kristjanssonii* 177R1B (SEQ ID NO:52); *C. hydrothermalis* 108 (SEQ ID NO:53); and *Anabaena variabilis* (SEQ ID NO:54).

M.CbeI was annotated as a D12 class N6 adenine-specific DNA methyltransferase in GenBank, but our analysis clearly shows that it functions as a cytosine specific methyltransferase. Like all known methyltransferases it contains a conserved F_G_G amino acid motif that facilitates interaction with S-adenosylmethionine, the source of the methyl group in these reactions. M.CbeI also contains a DPPY motif typical of N6-adenine methyltransferases, all of which contain a (D/N)PP(Y/F) motif (Malone et al., 1995 J Mol Biol 253(4): 618-32). Its SPP(Y/F) motif is the hallmark of N4 cytosine methyltransferases active site (Klimasauskas et al., 1989 Nucleic Acids Res 17(23):9823-32), making M.CbeI unusual in that it contains a DPPY motif in the active site (FIG. 10). Furthermore, the M.CbeI protein has no reported significant sequence or structural similarity to any characterized N4 cytosine methyltransferase. M.CbeI possesses some similarity to DmtB from *Anabaena variabilis* ATCC 29413 (FIG. 10), which has been shown to have m4C methyltransferase activity specific to the inner cytosine in the 5'-GGCC-3' recognition sequence. These proteins, which show 57% amino acid identity, represent a new α-class methyltransferase specific for GGCC sequence, different from the previously characterized β-class of N4 methyltransferases in hyperthermophiles, M.SuaI and M.PhoI, isolated from the archaea *Sulfolobus acidocaldarius* and *Pyrococcus horikoshii* OT3, respectively. M.CbeI is the first characterized α-class m4C methyltransferase from a hyperthermophile. Homologs exist in two other *Caldicellulosiruptor* species, Calhy 0409 (88% of protein sequence identity) from *C. hydrothermalis* 108 and Calkr 2088 (85% of protein sequence identity) from *C. kristjanssonii* 177R1B.

One reason that M.HaeIII is not sufficient to allow transformation of *C. bescii* even though it partially protects DNA from cleavage by CbeI may be the activity of CbeI itself. M.HaeIII-modified DNA ($m^5C$) was cleaved at reasonable efficiency by purified SuaI, a GGCC specific restriction enzyme completely blocked by m4C methylation at the inner cytosine residue in high concentrations. M.HaeIII is also known to have a significant level of promiscuous methylation activity at non-canonical sites and may actually increase restriction activity in vector DNA by methyl-directed restriction enzymes.

Efforts to optimize the transformation procedure for *C. bescii* have included adding cell wall weakening agents (isoniacin or glycine) during cell growth, altering temperature during the preparation of electro-competent cells, changing the composition of the washing and electroporation buffers, altering incubation times and temperatures of the cells with DNA prior to electric-pulse, varying the electrical settings during the electric pulse, and altering the composition of the recovery medium and incubation period before plating onto selective medium.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Materials and Methods

Strains and Growth Conditions.

All *Caldicellulosiruptor* species were grown in the DSMZ 516 medium (Svetlichnyi et al., 1990 Mikrobiologiya 59:598-604) with the following modifications. The mineral solution contained the following (per liter): $NH_4Cl$, 0.25 g; $KH_2PO_4$, 0.33 g; KCl, 0.33 g; $MgCl_2.6H_2O$, 0.33 g; $CaCl_2.2H_2O$, 0.33 g; yeast extract, 0.5 g; casein hydrolysate (enzymatic; US Biochemicals; Cleveland, Ohio), 5 g; cellobiose, 5 g; resazurin, 0.25 mg; vitamin solution, 2 ml; trace minerals solution, 1 ml; amino acid solution, 40 ml. The vitamin solution contained the following (per liter): biotin, 10 mg; folic acid, 10 mg; pyridoxine-HCl, 500 mg; thiamine-HCl, 25 mg; riboflavin, 25 mg; nicotinic acid, 25 mg; calcium pantothenate, 25 mg; vitamin $B_{12}$, 500 mg; p-aminobenzoic acid, 25 mg; lipoic acid, 25 mg. The trace element solution contained the following (per liter): HCl (25%:7.7M), 1.0 ml; $FeCl_3.4H_2O$, 2 g; $ZnCl_2$, 50 mg; $MnCl_2.4H_2O$, 50 mg; $H_3BO_3$, 50 mg; $CoCl_2.6H_2O$, 50 mg; $CuCl_2.2H_2O$, 30 mg; $NiCl_2.6H_2O$, 50 mg; $Na_4EDTA$ (tetrasodium salt), 50 mg; $(NH_4)_2MoO_4$, 50 mg; $AlK(SO_4)_2.12H_2O$, 50 mg. The amino acid solution contained the following (per liter): L-alanine, 1.9 g; L-arginine, 3.1 g; L-asparagine, 2.5 g; L-aspartic acid, 1.2; L-glutamic acid, 5.0 g; L-glutamine, 1.2 g; glycine, 5.0 g; L-histidine, 2.5 g; L-isoleucine, 2.5 g; L-leucine, 2.5 g; L-lysine, 2.5 g; L-methionine, 1.9 g; L-phenylalanine, 1.9 g; L-proline, 3.1 g; L-serine, 1.9 g; L-threonine, 2.5 g; L-tryptophan, 1.9 g; L-tyrosine, 0.3 g; L-valine, 1.3 g. The medium was prepared anaerobically under an argon atmosphere, $NaHCO_3$ (2 g/l) was added, and the mixture was reduced using 3 g/l cysteine and 1 g/l $Na_2S$. The final pH was 6.4. The medium was filtered sterilized using a 0.22-μm-pore-size sterile filter (Millipore Filter Corp., Bedford, Mass.). Cultures were incubated anaerobically overnight at the optimal temperature for each: *C. saccharolyticus* DSM 8903, 70° C.; *C. hydrothermalis* DSM 18901, 65° C.; *C. kristjanssonii* DSM 12137, 78° C.; *C. bescii* DSM 6925, 78° C.; *C. kronotskyensis* DSM 18902, 70° C.; *C. lactoaceticus* DSM 9545, 68° C.; *C. obsidiansis* ATCC BAA-2073, 78° C. *E. coli* strain JW 261 (pDCW 68, apramycin$^r$) was grown in LB broth supplemented with apramycin (50 μg/ml) with shaking at 37° C. overnight. Chromosomal DNA from *C. bescii* DSM 6725 was extracted using the DNeasy® Blood & Tissue Kit (Qiagen; Valencia, Calif.) according to the manufacturer's instructions. The two native plasmids (pATHE01 and pATRE02) in *C. bescii* were isolated using the method described by O'Sullivan and Klaenhammer (O'Sullivan and Klaenhammer, 1993 Appl Environ Microbiol 59:2730-2733) with the following modifications: 200 ml of mid-log phase *C. bescii* cultures were harvested by centrifugation at 3500×g for 15 minutes and suspended in Lysis buffer (containing 25% sucrose and 25 mg/ml lysozyme to enhance the cell wall degradation). pDCW68 DNA was isolated from *E. coli* using a Qiagen Mini-prep Kit.

Plasmid Constructions.

All primers used in these constructions are listed in Table 1. pJHW006 was constructed from pSET152 (GenBank: AJ414670.1) to replace the ColEI origin of replication with the pSC101 origin. The pSC101 origin was amplified from pWSK29 (GenBank: AF016889.1) using primers JH012 with an XbaI site and primer JH013 with a KpnI site. The pSC101 containing fragment and the pSET vector digested with XbaI and KpnI were ligated to form pJHW006. Construction of pDCW68, designed for transformation of *C. bescii*, required three cloning steps as well as overlapping PCR reactions. All PCR amplifications were performed using Pfu Turbo DNA polymerase (Agilent Technologies; Santa Clara, Calif. Technologies). A 3.936 kb PCR product containing the pSC101 replication origin, the apramycin resistance gene and the oriT (origin of transfer) was amplified from pJHW006 using primers DC176 and DC165 which contains a BamHI site. A 3.121 kb PCR product containing the pyrBCF region of the *C. bescii* genome was amplified from chromosomal DNA using primers DC188 and DC156 which also contained a BamHI site. The two PCR products were digested with BamHI and ligated to generate a 7.057 kb product. A 0.205-kb PCR product containing the regulatory region of a ribosomal protein (Cbes 2105) was amplified using primers DC175 containing an NheI site, and DC187 using chromosomal DNA as template. A 7.066-kb fragment was amplified from the 7.057 kb product using primers DC188 and DC176 and ligated to the 0.205-kb fragment that had been digested by NheI generating a 7.262-kb product. A 2.067-kb PCR fragment containing the 3' flanking region of the tryptophan synthase, alpha subunit (Cbes 1690) was amplified from chromosomal DNA using primers JF283 and JF287 and joined to a 2.045-kb kb PCR product containing the 5' flanking region of tryptophan synthase, alpha subunit (Cbes 1690) amplified from chromosomal DNA using DC182 which contained an AatII site and an overlapping primer JF286 using the high fidelity Pfu DNA polymerase (Agilent Technologies; Santa Clara, Calif. Technologies). A 4.112-kb product was then generated by overlapping PCR using the two fragments and *C. bescii* genomic DNA as a template. The 7.262-kb product from the second cloning step was amplified by PCR using DC180 which contains an AatII and DC100. The 7.262-kb product and the overlapping product were digested with AatII and ligated to yield pDCW68 (11.368 kb). To construct pDCW72, the 0.981 kb CbeI (Cbes 2438) open reading frame was amplified by PCR using primers DC216 and DC217 using *C. bescii* genomic DNA as template. The PCR product was digested with NcoI and XhoI and ligated to pET24d (Hethke et al., 1996 Nucleic Acids Res 24:2369-2376), which had also been digested with NcoI and XhoI. This vector contains a his-tag sequence that is added to the C-terminus of the expressed protein. The final plasmid was sequenced to confirm that the cloned cbeI gene was in frame with the C-terminal His-tag followed by a translation stop codon.

TABLE 1

| Primer | 5' → 3' | SEQ ID NO: |
|---|---|---|
| JH012 | AGAGAGTCTAGAGGCCTTTTGCTCACATGCGTT | 1 |
| JH013 | AGAGAGGGTACCAGGATCTCAAGAAGATCCTTTGAT | 2 |
| DC100 | TAGTCTTGATGCTTCACTGATAG | 3 |
| DC156 | AGAGGATCCTTAAGAGATTGCTGCGTTGATA | 4 |
| DC165 | ACAGGATCCAGCTTTAATGCGGTAGTTTATCACA | 5 |
| DC175 | AGAGCTAGCTTCAACAACCAGAGACACTTGGGA | 6 |
| DC176 | TCTGCTAGCTCCAACGTCATCTCGTTCTC | 7 |
| DC180 | TCTGACGTCATCTTTTCCGCTGCATAACCCT | 8 |
| DC182 | AGAGACGTCAATTGAAAAGCTTTAAAGTGTGGTGCA | 9 |

TABLE 1-continued

| Primer | 5' → 3' | SEQ ID NO: |
|---|---|---|
| DC187 | CATATTGACCATCCTTTCTATGTAGA | 10 |
| DC188 | TTGAAACATTTGCTTGGGCTAAG | 11 |
| DC216 | ACAACCATGGACCAAACCGCAAAAGGAAA | 12 |
| DC217 | TCTCCTCGAGCTCCCAACTTTCAATGTGAGAA | 13 |
| DC222 | TACAAGAAAAGCCCGTCAC | 14 |
| DC224 | AGCTAACAATTGAGTTTACACGT | 15 |
| JF283 | TGCAGTGTATAGCATGCAAAGCCTG | 16 |
| JF286 | ATCCCCTTAAATTTATTTGTCTTTTAG | 17 |
| JF287 | TTTGGAAGGATGATGAACTATGAATC | 18 |

Preparation of Cell Extracts and DNA Substrates.

A cell free extract of *C. bescii* was prepared from a 500 ml culture grown to mid-log phase, harvested by centrifugation at 6,000 g at 4° C. for 15 minutes and resuspended in CelLytic B Cell Lysis Reagent (Sigma-Aldrich; St. Louis, Mo.) containing a protease inhibitor cocktail (Complete, EDTA-free from Roche; Madison, Wis.). Extracts were sonicated on ice and then centrifuged at 13,000 rpm for 15 minutes at 4° C. Supernatants were removed and used immediately for enzyme activity assays. Protein concentrations were determined using the Bio-Rad protein assay kit with bovine serum albumin as the standard.

For in vitro methylation of DNA, pDCW68 DNA (20 µg), isolated from *E. coli* DH5α (dam$^+$, dcm$^+$), was treated with HaeIII Methyltransferase (New England Biolabs; Ipswich, Mass.) according to the suppliers instructions. To allow complete methylation, an additional 10 units of M.HaeIII and 80 µM S-adenosylmethionine (SAM) was added to the reaction every four hours of incubation at 37° C. for a total of 12 hours. The methyltransferase was inactivated by incubation at 65° C. for 15 minutes. Methylated DNA was purified and concentrated using the DNA Clean & Concentrator™-25 Kit (Zymo Research; Irvine, Calif.). The extent of protection was determined using HaeIII (New England Biolabs; Ipswich, Mass.) according to the supplier's instructions.

The 2.56 kb fragment containing three HaeIII (5'-GGCC-3') sites used in assays with purified CbeI was generated by PCR amplification using primers DC222 and DC224 (Table 1) from pDCW68 template. PCR products were purified and concentrated by Qiaquick PCR Purification Kit (Qiagen; Valencia, Calif.) prior to use in the restriction assays.

Endonuclease Assays.

Reactions were performed in 60 µl volumes at 75° C. using 0.5 µg to 1.0 µg of the DNA substrate: pDCW68, methylated pDCW68, pATHE 01, or pATHE 02. For cell free extracts, 4 µg of total cell protein was incubated at 75° C. in reaction buffer (10 mM Tris-HCl, pH 6.7, buffer containing 50 mM NaCl, 10 mM MgCl$_2$, 1 mM dithioerythritol, 0.01% BSA). Samples (10 µl) were withdrawn at various time points, mixed with 6×DNA gel-loading buffer (0.25% Bromophenol blue and Xylene Cyanol, 18 mM EDTA, and 30% of Glycerol), and then chilled to −20° C. to stop the reaction. The cleavage products were separated electrophoretically on a 1.2% agarose gel.

Preparation of Assay of Purified CbeI Protein.

BL21-CodonPlus(DE3)-RILP cells (Agilent Technologies; Santa Clara, Calif. Technologies) were used for recombinant protein expression. Cells were grown at 23° C. in LB broth supplemented with kanamycin (25 µg/ml) and chloramphenicol (50 µg/ml) to $O.D_{260}$ 0.6 and induced by the addition of 0.5 mM IPTG at 23° C. for overnight. Cells were harvested by centrifugation, resuspended in CelLytic B Cell Lysis Reagent (Sigma-Aldrich; St. Louis, Mo.) containing protease inhibitor (Complete, EDTA-free from Roche; Madison, Wis.) and lysed by sonication. All purification steps were done at 4° C. using the Ni-NTA Spin Kit (Qiagen; Valencia, Calif.) following manufacturer's instruction. Protein concentrations were determined by Bio-Rad protein assay kit as described above. SDS/PAGE and Coomassie brilliant blue G-250 staining were as described (Sedmak and Grossberg, 1977 Anal Biochem 79:544-552). Enzyme assays with purified CbeI were carried out in 10 µl reaction volumes with NEBuffer 4 (20 mM Tris-acetate pH 7.9, 50 mM potassium acetate, 10 mM magnesium acetate, 1 mM dithiothreitol) and 200 ng of DNA substrate. The amount of purified CbeI protein used in each reaction varied depending on the experiment and is indicated.

Bioinformatic Analysis.

To produce an alignment and phylogenetic tree of 46 amino acid sequences of HaeIII-like proteins, we used ClustalW, version 2 (Larkin et al., 2007 Bioinformatics 23:2947-2948) which is based on the neighbor-joining (NJ) method used for phylogenetic calculations. The tree was visualized with TreeView (Page, 1996 Comput Appl Biosci 12:357-358). To discover conserved motifs of groups of HaeIII-like protein sequences, we used MEME (Bailey and Elkan, 1994 Proc Int Conf Intell Syst Mol Biol 2:28-36) and GLAM2 (Frith et al., 2008 PLoS Comput Biol 4:e1000071). Default parameters were used for all analyses.

Identification of the CbeI Cleavage Site.

DNA fragments resulting from digestion by either HaeIII or CbeI were separated electrophoretically and extracted from the gel matrix using a QIAquick Gel Extraction Kit (Qiagen; Valencia, Calif.). The products were then cloned into pWSK29 (Wang and Kushner, 1991 Gene 100:195-199), which had been digested with EcoRV, using the Fast-Link™ DNA ligation kit (Epicentre Biotechnologies) and sequenced.

Determination of the Site of DNA Methylation by M.CbeI.

Using the method of Bart et al. (Bart et al., 2005 Nucleic Acids Res 33:e124) we determined the site of methylation by M.CbeI. This method allow the detection of DNA methylation by comparing sequencing traces in Sanger sequencing reactions between methylated and unmethyltaed DNA. The peak height of G bases incorporated to pair with N4m-Cytosine is higher than if the cytosine is unmethylated. UC18 plasmid DNA isolated from *E. coli* (DH5α: dam$^+$, dcm$^+$), untreated or methylated with M.CbeI or M.HaeIII was used in the SeqDoC program (Crowe, 2005 BMC Bioinformatics 6:133). The sequences were used to align traces and visually display the difference in corresponding peak heights between traces. There is a clear pattern that the second G in GGCC sequences is higher in M.CbeI treated plasmid, as compared to untreated. M.HaeIII treated plasmid does not appear significantly different. This confirms that M.CbeI methylates the N4 position of cytosine.

Example 2

Preparation of C. bescii "Competent" Cells 2.5 ml of *Caldicellulosiruptor* species from an overnight culture are inoculated into bottles of 500 ml of appropriate medium (either Defined or Defined+Uracil). The cells are incubated at optimal temperature (78° C.) up to mid-log phase (as determined by either measuring Moo to 0.1 or by cell counts $2 \times 10^7$ cells/ml). The cells are centrifuged at 4500×g for 15 minutes at 25° C. and the supernatant is decanted. The pelleted cells are resuspended in 50 ml of ice cold 10% sucrose. The cells are washed by twice re-centrifuging and resuspending in 10% as just described.

The washed cells pellets are resuspended in a total volume of 500 µl of ice cold 10% Sucrose after the final wash. Aliquots of 40-50 µl of the resuspended cells are placed into cold microfuge tubes and flash frozen by dipping them into a dry ice and ethanol mix.

Transformation Protocol

DNA (0.5-1.0 µg) is added to competent cells, mixed gently, and incubated for 10 minutes on ice. For natural transformation, the mixed competent cells are injected into 10 ml of pre-warmed complex medium (per 1 liter of medium: 20 ml of 50× salts, 2 ml of 500× vitamin mix, 1 ml of 1000× trace minerals, 40 ml of 25× amino acid solution, 50 µl. of 5 mg/ml resazurin, 50 ml of 10% cellobiose, 2.4 ml of 1 M $KH_2PO_4$, 5 ml of 10% yeast extract, and 50 ml of 10% casein hydrolysate) at 75° C., and then incubated at the optimal temperature for the given species overnight. For electrotransformation, the electroporation of mixed competent cells was performed via single electric pulse (1.0 kV, 600Ω, and 25 mF) in 1 mm cuvettes using a Bio-Rad gene Pulser, and then incubated in 10 ml of complex medium at optimal temperature overnight.

After overnight incubation, the 10 ml recovery culture is centrifuged at 3500×g for 10 minutes and the cell pellet is washed twice with 1×AT base salts. After washing, the cells are suspended in 0.28 ml of 1×AT base salts. 100 µl of the cell suspension is placed into 4 ml of overlay solution (1.0% agar in water) and the overlay suspension is spread onto an appropriate selective medium. The plates are placed in a jar, degassed, and observed for growth after incubation for four days at 75° C.

Example 3

TABLE 2

Strains/plasmids used and constructed.

| Strains/Plasmids | Description | Source |
|---|---|---|
| Strains | | |
| DSM 6725[a] | Re-classified as *Caldicellulosiruptor bescii* (Yang et al., 2010 Int J Syst Evol Microbiol. 60(Pt 9): 2011-5)/Wild type (ura$^+$/5-FOA$^S$) | DSMZ[c] |
| JWCB 002[a] | pyrΔBCF (partial deletion in pyrB and pyrF, and entire deletion of pyrC/(ura$^-$/5-FOA$^R$) | This study |

TABLE 2-continued

Strains/plasmids used and constructed.

| Strains/Plasmids | Description | Source |
|---|---|---|
| JWCB 005[a] | Recover to wild type by homologous recombination/gene replacement between pDCW 70 and JWCB 002/(ura+/5-FOA[S]) | This study |
| JW 284[b] | Cbes_2437 (M.CbeI) expression strain/Kanamycin[R], Spectinomycin[R], Chloramphenicol[R] | This study |
| Plasmids | | |
| pDCW 70 | Integrating vector to gene replacement in pyrBCF locus in JWCB002/Apramycin[R] | This study |
| pDCW 73 | M.CbeI Expression vector/Kanamycin[R], Spectinomycin[R], Chloramphenicol[R] | This study |

Strains and Growth Conditions

Caldicellulosiruptor species were grown in modified DSMZ 516 medium (Chung et al., 2011 J Ind Microbiol Biotechnol 38:1867-1877) at a final pH 6.8. Liquid cultures were inoculated with a 1-2% inoculum or with a single colony and then incubated at 75° C. overnight in anaerobic culture bottles or Hungate tubes degassed with at least three cycles of vacuum and argon. A solid medium was prepared by mixing an equal volume of liquid medium at a 2× concentration with 1% (wt/vol) Phytagel (Sigma-Aldrich; St. Louis, Mo.) previously autoclaved to solubilize. Both solutions were maintained at 95° C. and poured into petri dishes immediately after mixing. Initial plating of C. bescii in soft agar overlays allowed the cells to grow but they did not form discrete colonies because of the soft and liquid nature of the agar matrix. Increasing the agar concentration from 0.3% to 1.5% in the overlay allowed both abundant growth and the isolation of discrete colonies. Cells from overnight cultures were pelleted, washed in 1× base salts (Chung et al., 2011 J Ind Microbiol Biotechnol 38:1867-1877) three times and resuspended in 300-500 µl of 1× base salts. 100 µl of the cell suspension was mixed with 4 ml of soft top agar (1.5%) and poured across the top of a solid medium Plates were incubated in anaerobic jars degassed with at least three cycles of vacuum and argon at 75° C. for 3 to 5 days. E. coli strains, DH5α (dam+dcm+), BL21 (dam+dcm+), or ET12567 (dam−dcm−) were used to prepare pDCW70 DNA. Cells were grown in LB broth supplemented with apramycin (50 µg/ml) and plasmid DNA was isolated using a Qiagen; Valencia, Calif. Mini-prep Kit. Chromosomal DNA from C. bescii DSM 6725 was extracted using the Quick-gDNA™ MiniPrep (Zymo) according to the manufacturer's instructions.

Isolation and Characterization of 5-FOA Resistant/Uracil Auxotrophic Mutants

C. bescii DSM 6725 was inoculated into 10 ml of modified DSMZ 516 medium and grown anaerobically at 60° C. for 24 hours. Cells were harvested at 18,000×g for five minutes, washed twice with mineral solution (Chung et al., 2011 J Ind Microbiol Biotechnol 38:1867-1877), resuspended in 1 ml of mineral solution and plated by mixing 100 µl of cells with 4 ml of 0.3% agar and overlaying onto defined modified DSMZ 516 agar medium (no yeast extract or casein) supplemented with 20 µM uracil and 8 mM 5-FOA (US Biologicals; Swampscott, Mass.). The plates were incubated anaerobically at 60° C. for three days and 5-FOA resistant colonies were transferred to 10 ml of defined modified DSMZ 516 medium with 20 µM uracil and 8 mM 5-FOA and incubated overnight at 75° C. anaerobically. To test for uracil auxotrophy, cells were subcultured in defined modified DSMZ 516 medium with or without uracil (20 µM). Cell number was measured in a Petroff Houser counting chamber using a phase-contrast microscope with 40× magnification.

Plasmid Construction and DNA Manipulation

Primers used in these constructions are listed in Table 4. All PCR amplifications were performed using Pfu Turbo DNA polymerase (Agilent Technologies; Santa Clara, Calif. Technologies). A 1.858 kb fragment containing the pSC101 replication origin was amplified from pDCW68 (Chung et al., 2011 J Ind Microbiol Biotechnol 38:1867-1877) using primers DC081 and DC230, which contain KpnI and AatII sites, respectively. A 4.343 kb fragment containing the apramycin resistance and pyrBCF cassettes was amplified from pDCW68 using primers DC084 and DC232 to which an AatII and KpnI site had been added. An additional fragment (1.801 kb) containing DNA sequences not relevant to the experiments described here was amplified using primers DC212 and DC213. These three DNA fragments were cut by restriction enzymes, KpnI and AatII, and then ligated to yield pDCW69 (8.014 kb). pDCW70 was constructed by introducing a single nucleotide change (an A to C transversion) in the +978 amino acid of pyrC (Cbes 1376) ORF using "PCR based Site Directed Mutagenesis", using DC 214 and DC 215 primers, to create the KpnI site (GGTAC/C), in pDCW 69. To construct pDCW73, the 0.837 kb M.CbeI (Cbes 2437) open reading frame was amplified by PCR using primers DC238 and DC239 using C. bescii genomic DNA as template. The PCR product was digested with BamHI and XhoI and ligated to pET24d (Hethke et al., 1996 Nucleic Acids Res 24(12): 2369-76), which had also been digested with BamHI and XhoI. This vector contains a His-tag sequence that is added to the C-terminus of the expressed protein. All plasmids used in this study were sequenced to confirm their structure.

Purification of His-Tagged M.CbeI and In Vitro Methylation of DNA

Purification of M.CbeI was similar to the method described by Chung et al. (Chung et al., 2011 J Ind Microbiol Biotechnol 38:1867-1877). BL21-CodonPlus(DE3)-RILP cells (Agilent Technologies; Santa Clara, Calif. Technologies), containing pDCW73, was used for M.CbeI protein expression. Cells were grown at 23° C. in LB broth supplemented with kanamycin (25 µg/ml) and chloramphenicol (50 µg/ml) to $OD_{600}$ 0.7 and induced by addition of 0.5 mM isopropyl b-D-1-thiogalactopyranoside (IPTG) at 23° C. overnight. His-tagged (carboxy terminus) M.CbeI was purified as described previously (Chung et al., 2011 J Ind Microbiol Biotechnol 38:1867-1877) except for the use of a His-Spin Protein Miniprep™ (Zymo Research; Irvine, Calif.). Protein concentration was determined by the Bio-Rad protein assay using bovine serum albumin (BSA) as the standard. Purified protein was displayed using sodium dodecyl sulfate polyacrylamide gel electrophoresis (SDS-PAGE, 1996 Comput Appl Biosci 12(4):357-8) and stained with Coomassie brilliant blue G-250 as described (Sedmak and Grossberg, 1977 Anal Biochem 79(1-2):544-52). Protein purity was determined to be >98%.

For in vitro methylation, DNA isolated from *E. coli* DH5α (dam⁺dcm⁺) was treated with either M.CbeI or M.HaeIII methyltransferase (NEB). 50 ng of purified M.CbeI was incubated with 50 mM Tris-HCl, 50 mM NaCl, 80 µM S-adenosylmethionine (SAM, Samuelson and Xu, 2002 J Mol Biol 319(3):673-83), 10 mM Dithiothreitol (DTT) at pH 8.5 and 20 µg of DNA substrate in 400 µl reaction, and incubate for two hours at 78° C. The M.HaeIII methylation reaction was performed according supplier's instructions. To allow complete methylation, an additional 10 units of M.HaeIII and 80 µM SAM was added to the reaction every four hours of incubation at 37° C. for a total of 12 hours. Methylated DNAs were purified and concentrated by Phenol/Chloroform extraction and ethanol precipitation. The extent of protection was determined by cleavage using HaeIII and NotI (NEB) restriction enzymes according to the supplier's instructions.

Analysis of Methylation by M.CbeI

To identify the site of methylation by M.CbeI, pre-modified DNA was compared to that after methylation and the changes were determined by direct visualization in automated DNA sequencing chromatograms (Rao and Buckler-White, 1998 Nucleic Acids Res 26(10):2505-7; Bart et al., 2005 Nucleic Acids Res 33(14):e124). In vitro methylation of pUC18 DNA isolated from *E. Coli* DH5α (dam⁺dcm⁺) was carried out using M.HaeIII (NEB) and purified M.CbeI. The efficiency of methylation was determined by cleavage of the methylated and unmethylated DNA with HaeIII (NEB), purified CbeI, and *C. bescii* cell free extracts (CFE). Digested DNA was displayed by agarose gel electrophoresis and visualization using ethidium bromide staining. Automatic sequencing was performed using primers M13F(–20) and M13R(–20) in an ABI automated PRISM big-dye-terminator system (Macrogen, Inc.; Rockville, Md.). Sequences were analyzed using the Chromas Lite v2.01 (Technelysium Pty Ltd.) and ABI chromatograms were compared by aligning the Sequencing traces and using SeqDoc (Crowe, 2005 BMC Bioinformatics 6:133).

Transformation of *C. bescii*

To prepare cells for transformation, 2.5 milliliter of a freshly grown JWCB002 (ΔpyrBCF) culture was inoculated into 500 ml of fresh medium, and incubated at 78° C. to mid-log phase (O.D.₆₀₀-0.1 or 2×10⁷ cells/ml). The cultures were cooled to room temperature for 1 hour, harvested by centrifugation (5000×g, 15 minutes) at 25° C. and washed twice with 250 ml of pre-chilled 10% sucrose. After the final wash, the cell pellets were resuspended in a total volume of 1 ml of pre-chilled 10% sucrose and aliquots of 50 µl were freeze-dried in microcentrifuge tubes in a dry ice/ethanol bath. Plasmid DNA (0.5-1.0 µg) was added to cells, gently mixed and incubated in 10% sucrose for 15 minutes at room temperature. Electrotransformation of the cell/DNA mixture was performed via single electric pulse (1.8 kV, 600Ω, and 25 µF) in a pre-chilled 1 mm cuvette using a Bio-Rad gene Pulser. After pulsing, cells were incubated overnight at 75° C. in 10 ml modified DSMZ 516 medium supplemented with 20 µM of uracil, harvested by centrifugation (at 5000×g for 20 minutes) and resuspended in 1 ml of 1× base salt. A cell suspension (100 microliters) was plated onto defined medium without uracil. A solid defined modified DSMZ 516 medium (no yeast extract and casein) was prepared by mixing an equal volume of 2× liquid medium with 1% (wt/vol) previously autoclaved Phytagel (Sigma-Aldrich; St. Louis, Mo.). Both solutions were maintained at 95° C. prior to mixing and immediately poured into petri dishes. Transformation mixtures were incubated overnight at 78° C. in 10 ml modified DSMZ 516 medium supplemented with uracil. Cells were harvested by centrifugation, resuspended in 1 ml of 1× base salt (Chung et al., 2011 J Ind Microbiol Biotechnol 38:1867-1877), (100 microliters) mixed with 4 ml of soft agar (0.3% agar), that had been melted at 100° C. and cooled in a 45° C. heating block and plated onto defined medium without uracil. Plates were incubated in anaerobic jars at 75° C. for three to four days. To confirm marker replacement of the pyrBCF region in the transformants, DNA from uracil prototrophic transformants was used to amplify the chromosomal region using primers DC163 and DC188 which anneal outside the regions of the pyrBCF fragment contained on pDCW70. PCR products of this locus amplified from the wild type, the deletion mutant and the transformants were digested with Kpn1 and sequenced.

RNA Extraction and RT-qPCR Analyses

Total RNA was extracted using an RNeasy Mini kit (Qiagen; Valencia, Calif.) and stored at –80° C. RNA was treated with RNase-free DNase (Qiagen; Valencia, Calif.) according to manufacturer's instructions. cDNA was then prepared using the AffinityScript quantitative PCR (qPCR) cDNA synthesis kit (Agilent Technologies; Santa Clara, Calif. Technologies). All quantitative reverse transcription-PCR (RT-qPCR) experiments were carried out with an Mx3000P instrument (Stratagene; a part of Agilent Technologies; Santa Clara, Calif.) with the Brilliant SYBR green qPCR master mix (Agilent Technologies; Santa Clara, Calif. Technologies). The gene encoding pyruvate ferredoxin oxidoreductase (Cbes 0876) was used as an internal control for RNA. The primers used in RT-qPCR experiments are listed in Table 4.

TABLE 3

Influence of different methylation status on pDCW70 in transformation efficiency into JWCB002 (ΔpyrBCF) strain.

| *E. coli* strain as source of pDCW70/ Methylation status | Transformation efficiency (Transformants/µg of DNA)[a] |
|---|---|
| DH5α (dam⁺dcm⁺) | ND[b] |
| BL21 (dam⁺dcm⁻) | ND[b] |
| ET12567 (dam⁻dcm⁻) | ND[b] |
| DH5α (dam⁺dcm⁺)/M.HaeIII | ND[b] |
| DH5α (dam⁺dcm⁺)/M.CbeI | ~50[c] |

[a]Each transformation experiment used approximately 10⁹ cells and 600 ng of transforming DNA
[b]ND (Not detected): based on at least 30 independent transformation experiments.
[c]Average of the results of five independent transformation experiments.

TABLE 4

Primers

| Primers | Sequences (5' → 3") | SEQ ID NO: |
|---|---|---|
| DC081 | ACCAGCCTAACTTCGATCATTGGA | 19 |
| DC084 | TCTGACGCTCAGTGGAACGAA | 20 |
| DC156 | TTAAGAGATTGCTGCGTTGATA | 21 |
| DC163 | TCCTGAACCAATAACCAAAACCT | 22 |
| DC188 | TTGAAACATTTGCTTGGGCTAAGA | 23 |
| DC212 | ACCCTCAAATATAACACAAAAATTGTCCAC | 24 |

TABLE 4-continued

Primers

| Primers | Sequences (5' → 3") | SEQ ID NO: |
|---|---|---|
| DC213 | GTTATTATTCTCTGTGGATAAGTC | 25 |
| DC214 | AGCGGTACCATTGGGTTTGAGAC | 26 |
| DC215 | TGCAGCAAGGTTAAATTCGACATT | 27 |
| DC230 | TCATCTGTGCATATGGACAG | 28 |
| DC232 | TAAGAGATTGCTGCGTTGATA | 29 |
| DC238 | AGAGGATCCATGCTCAAAAACGTTCTTCGATAC | 30 |
| DC239 | TCTCCTCGAGCAGACCAAGTGCGTATTTTTC | 31 |
| DC326 | TCAGGTCCTGCTATAAAGCCAA | 32 |
| DC329 | AGGTGTTTGAGAGATTTCCAAGG | 33 |
| M13F(-20) | GTAAAACGACGGCCAGT | 34 |
| M13R(-20) | GCGGATAACAATTTCACACAGG | 35 |

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of transforming a microbial cell, the method comprising:
   treating a DNA molecule comprising at least one 5'-GGCC-3' sequence with a M.CbeI polypeptide under condition effective for the M.CbeI polypeptide to methylate at least one C residue of the 5'-GGCC-3' sequence;
   introducing the methylated polynucleotide into the microbial cell that comprises a thermophile or a hyperthermophile.

2. The method of claim 1 wherein the microbial cell comprises a *Caldicellulosiruptor* spp.

3. The method of claim 2 wherein the *Caldicellulosiruptor* spp. comprises *C. bescii*.

4. The method of claim 1 wherein the DNA is treated with the M.CbeI in vitro.

5. A genetically modified *Caldicellulosiruptor* spp. cell comprising a heterologous polynucleotide comprising at least one 5'-GGCC-3' sequence comprising at least one methylated C residue.

6. The genetically modified cell of claim 5 wherein the heterologous polynucleotide was methylated in vitro by a M.CbeI polypeptide.

7. The genetically modified cell of claim 5 wherein the *Caldicellulosiruptor* spp. comprises *C. bescii*.

* * * * *

UNITED STATES PATENT AND TRADEMARK OFFICE
CERTIFICATE OF CORRECTION

| | |
|---|---|
| PATENT NO. | : 8,962,333 B2 |
| APPLICATION NO. | : 13/439069 |
| DATED | : February 24, 2015 |
| INVENTOR(S) | : Westpheling et al. |

Page 1 of 1

It is certified that error appears in the above-identified patent and that said Letters Patent is hereby corrected as shown below:

In the Specification

Column 1, line 14, under GOVERNMENT FUNDING

Please delete
"The present invention was made with government support under Grant No. DE-AC05-000R22725, awarded by the U.S. Department of Energy, BioEnergy Science Center. The Government has certain rights in this invention"

And insert
--This invention was made with government support under Grant No. DE-AC05-00OR22725, awarded by the U.S. Department of Energy, BioEnergy Science Center. The government has certain rights in the invention.--

Signed and Sealed this
Twenty-third Day of June, 2015

Michelle K. Lee
*Director of the United States Patent and Trademark Office*

SEQUENCE LISTING

```
<160> NUMBER OF SEQ ID NOS: 54

<210> SEQ ID NO 1
<211> LENGTH: 33
<212> TYPE: DNA
<213> ORGANISM: artificial
<220> FEATURE:
<223> OTHER INFORMATION: synthetic oligonucleotide primer

<400> SEQUENCE: 1
agagagtcta gaggcctttt gctcacatgc gtt                                    33

<210> SEQ ID NO 2
<211> LENGTH: 36
<212> TYPE: DNA
<213> ORGANISM: artificial
<220> FEATURE:
<223> OTHER INFORMATION: synthetic oligonucleotide primer

<400> SEQUENCE: 2
agagagggta ccaggatctc aagaagatcc tttgat                                 36

<210> SEQ ID NO 3
<211> LENGTH: 23
<212> TYPE: DNA
<213> ORGANISM: artificial
<220> FEATURE:
<223> OTHER INFORMATION: synthetic oligonucleotide primer

<400> SEQUENCE: 3
tagtcttgat gcttcactga tag                                               23
```

```
<210> SEQ ID NO 4
<211> LENGTH: 31
<212> TYPE: DNA
<213> ORGANISM: artificial
<220> FEATURE:
<223> OTHER INFORMATION: synthetic oligonucleotide primer

<400> SEQUENCE: 4
agaggatcct taagagattg ctgcgttgat a                               31

<210> SEQ ID NO 5
<211> LENGTH: 34
<212> TYPE: DNA
<213> ORGANISM: artificial
<220> FEATURE:
<223> OTHER INFORMATION: synthetic oligonucleotide primer

<400> SEQUENCE: 5
acaggatcca gctttaatgc ggtagtttat caca                            34

<210> SEQ ID NO 6
<211> LENGTH: 33
<212> TYPE: DNA
<213> ORGANISM: artificial
<220> FEATURE:
<223> OTHER INFORMATION: synthetic oligonucleotide primer

<400> SEQUENCE: 6
agagctagct tcaacaacca gagacacttg gga                             33

<210> SEQ ID NO 7
<211> LENGTH: 29
<212> TYPE: DNA
<213> ORGANISM: artificial
<220> FEATURE:
<223> OTHER INFORMATION: synthetic oligonucleotide primer

<400> SEQUENCE: 7
tctgctagct ccaacgtcat ctcgttctc                                  29

<210> SEQ ID NO 8
<211> LENGTH: 31
<212> TYPE: DNA
<213> ORGANISM: artificial
<220> FEATURE:
<223> OTHER INFORMATION: synthetic oligonucleotide primer

<400> SEQUENCE: 8
tctgacgtca tcttttccgc tgcataaccc t                               31

<210> SEQ ID NO 9
<211> LENGTH: 37
<212> TYPE: DNA
<213> ORGANISM: artificial
<220> FEATURE:
<223> OTHER INFORMATION: synthetic oligonucleotide primer

<400> SEQUENCE: 9
agagacgtca attgaaaaag ctttaaagtg tggtgca                         37

<210> SEQ ID NO 10
<211> LENGTH: 26
<212> TYPE: DNA
<213> ORGANISM: artificial
<220> FEATURE:
<223> OTHER INFORMATION: synthetic oligonucleotide primer
```

```
<400> SEQUENCE: 10
catattgacc atcctttcta tgtaga                                        26

<210> SEQ ID NO 11
<211> LENGTH: 23
<212> TYPE: DNA
<213> ORGANISM: artificial
<220> FEATURE:
<223> OTHER INFORMATION: synthetic oligonucleotide primer

<400> SEQUENCE: 11
ttgaaacatt tgcttgggct aag                                           23

<210> SEQ ID NO 12
<211> LENGTH: 29
<212> TYPE: DNA
<213> ORGANISM: artificial
<220> FEATURE:
<223> OTHER INFORMATION: synthetic oligonucleotide primer

<400> SEQUENCE: 12
acaaccatgg accaaaccgc aaaaggaaa                                     29

<210> SEQ ID NO 13
<211> LENGTH: 32
<212> TYPE: DNA
<213> ORGANISM: artificial
<220> FEATURE:
<223> OTHER INFORMATION: synthetic oligonucleotide primer

<400> SEQUENCE: 13
tctcctcgag ctcccaactt tcaatgtgag aa                                 32

<210> SEQ ID NO 14
<211> LENGTH: 19
<212> TYPE: DNA
<213> ORGANISM: artificial
<220> FEATURE:
<223> OTHER INFORMATION: synthetic oligonucleotide primer

<400> SEQUENCE: 14
tacaagaaaa gcccgtcac                                                19

<210> SEQ ID NO 15
<211> LENGTH: 23
<212> TYPE: DNA
<213> ORGANISM: artificial
<220> FEATURE:
<223> OTHER INFORMATION: synthetic oligonucleotide primer

<400> SEQUENCE: 15
agctaacaat tgagtttaca cgt                                           23

<210> SEQ ID NO 16
<211> LENGTH: 25
<212> TYPE: DNA
<213> ORGANISM: artificial
<220> FEATURE:
<223> OTHER INFORMATION: synthetic oligonucleotide primer

<400> SEQUENCE: 16
tgcagtgtat agcatgcaaa gcctg                                         25

<210> SEQ ID NO 17
```

```
<211> LENGTH: 27
<212> TYPE: DNA
<213> ORGANISM: artificial
<220> FEATURE:
<223> OTHER INFORMATION: synthetic oligonucleotide primer

<400> SEQUENCE: 17
atccccttaa atttatttgt cttttag                                        27

<210> SEQ ID NO 18
<211> LENGTH: 26
<212> TYPE: DNA
<213> ORGANISM: artificial
<220> FEATURE:
<223> OTHER INFORMATION: synthetic oligonucleotide primer

<400> SEQUENCE: 18
tttggaagga tgatgaacta tgaatc                                         26

<210> SEQ ID NO 19
<211> LENGTH: 24
<212> TYPE: DNA
<213> ORGANISM: artificial
<220> FEATURE:
<223> OTHER INFORMATION: synthetic oligonucleotide primer

<400> SEQUENCE: 19
accagcctaa cttcgatcat tgga                                           24

<210> SEQ ID NO 20
<211> LENGTH: 21
<212> TYPE: DNA
<213> ORGANISM: artificial
<220> FEATURE:
<223> OTHER INFORMATION: synthetic oligonucleotide primer

<400> SEQUENCE: 20
tctgacgctc agtggaacga a                                              21

<210> SEQ ID NO 21
<211> LENGTH: 22
<212> TYPE: DNA
<213> ORGANISM: artificial
<220> FEATURE:
<223> OTHER INFORMATION: synthetic oligonucleotide primer

<400> SEQUENCE: 21
ttaagagatt gctgcgttga ta                                             22

<210> SEQ ID NO 22
<211> LENGTH: 23
<212> TYPE: DNA
<213> ORGANISM: artificial
<220> FEATURE:
<223> OTHER INFORMATION: synthetic oligonucleotide primer

<400> SEQUENCE: 22
tcctgaacca ataaccaaaa cct                                            23

<210> SEQ ID NO 23
<211> LENGTH: 24
<212> TYPE: DNA
<213> ORGANISM: artificial
<220> FEATURE:
<223> OTHER INFORMATION: synthetic oligonucleotide primer

<400> SEQUENCE: 23
```

-continued ttgaaacatt tgcttgggct aaga                                          24

<210> SEQ ID NO 24
<211> LENGTH: 30
<212> TYPE: DNA
<213> ORGANISM: artificial
<220> FEATURE:
<223> OTHER INFORMATION: synthetic oligonucleotide primer

<400> SEQUENCE: 24
accctcaaat ataacacaaa aattgtccac                                    30

<210> SEQ ID NO 25
<211> LENGTH: 24
<212> TYPE: DNA
<213> ORGANISM: artificial
<220> FEATURE:
<223> OTHER INFORMATION: synthetic oligonucleotide primer

<400> SEQUENCE: 25
gttattattc tctgtggata agtc                                          24

<210> SEQ ID NO 26
<211> LENGTH: 23
<212> TYPE: DNA
<213> ORGANISM: artificial
<220> FEATURE:
<223> OTHER INFORMATION: synthetic oligonucleotide primer

<400> SEQUENCE: 26
agcggtacca ttgggtttga gac                                           23

<210> SEQ ID NO 27
<211> LENGTH: 24
<212> TYPE: DNA
<213> ORGANISM: artificial
<220> FEATURE:
<223> OTHER INFORMATION: synthetic oligonucleotide primer

<400> SEQUENCE: 27
tgcagcaagg ttaaattcga catt                                          24

<210> SEQ ID NO 28
<211> LENGTH: 20
<212> TYPE: DNA
<213> ORGANISM: artificial
<220> FEATURE:
<223> OTHER INFORMATION: synthetic oligonucleotide primer

<400> SEQUENCE: 28
tcatctgtgc atatggacag                                               20

<210> SEQ ID NO 29
<211> LENGTH: 21
<212> TYPE: DNA
<213> ORGANISM: artificial
<220> FEATURE:
<223> OTHER INFORMATION: synthetic oligonucleotide primer

<400> SEQUENCE: 29
taagagattg ctgcgttgat a                                             21

<210> SEQ ID NO 30
<211> LENGTH: 33
<212> TYPE: DNA

```
<213> ORGANISM: artificial
<220> FEATURE:
<223> OTHER INFORMATION: synthetic oligonucleotide primer

<400> SEQUENCE: 30
agaggatcca tgctcaaaaa cgttcttcga tac                                    33

<210> SEQ ID NO 31
<211> LENGTH: 31
<212> TYPE: DNA
<213> ORGANISM: artificial
<220> FEATURE:
<223> OTHER INFORMATION: synthetic oligonucleotide primer

<400> SEQUENCE: 31
tctcctcgag cagaccaagt gcgtattttt c                                      31

<210> SEQ ID NO 32
<211> LENGTH: 22
<212> TYPE: DNA
<213> ORGANISM: artificial
<220> FEATURE:
<223> OTHER INFORMATION: synthetic oligonucleotide primer

<400> SEQUENCE: 32
tcaggtcctg ctataaagcc aa                                                22

<210> SEQ ID NO 33
<211> LENGTH: 23
<212> TYPE: DNA
<213> ORGANISM: artificial
<220> FEATURE:
<223> OTHER INFORMATION: synthetic oligonucleotide primer

<400> SEQUENCE: 33
aggtgtttga gagatttcca agg                                               23

<210> SEQ ID NO 34
<211> LENGTH: 17
<212> TYPE: DNA
<213> ORGANISM: artificial
<220> FEATURE:
<223> OTHER INFORMATION: synthetic oligonucleotide primer

<400> SEQUENCE: 34
gtaaaacgac ggccagt                                                      17

<210> SEQ ID NO 35
<211> LENGTH: 22
<212> TYPE: DNA
<213> ORGANISM: artificial
<220> FEATURE:
<223> OTHER INFORMATION: synthetic oligonucleotide primer

<400> SEQUENCE: 35
gcggataaca atttcacaca gg                                                22

<210> SEQ ID NO 36
<211> LENGTH: 189
<212> TYPE: PRT
<213> ORGANISM: Caldicellulosiruptor bescii
<220> FEATURE:
<221> NAME/KEY: NON_CONS
<222> LOCATION: (49)..(50)
<220> FEATURE:
<221> NAME/KEY: NON_CONS
<222> LOCATION: (119)..(120)
```

<400> SEQUENCE: 36

| Ala | Ile | Arg | Ile | Leu | Glu | Pro | Ala | Thr | Lys | Trp | Glu | Ile | Gly | Ile | Ser |
|---|---|---|---|---|---|---|---|---|---|---|---|---|---|---|---|
| 1 | | | | 5 | | | | | 10 | | | | | 15 | |

Cys Lys His Asn His Leu Ala Val Lys His Pro Arg Leu Ser Pro Lys
           20             25             30

Leu Asp Phe Gly Lys Arg Trp Leu Gly Ile Pro Cys Ser Gln Asn Tyr
        35              40             45

Phe Glu Phe Lys Ile Gly Pro Lys Leu Lys Leu Pro Thr Lys Phe Gln
50                  55                  60

Asn Ile Tyr Phe Lys Glu Asp Ser Lys Asn Thr Val His Val Val Cys
65                  70                  75                  80

Asp Asn Gly Trp Thr Ile Ser Phe Arg Leu His Asn Ala Ser Ser Lys
                85                  90                  95

Leu Glu Leu Ser Leu Lys Phe Asp Ile Gln Leu Val Gly His Pro Gln
                100                 105                 110

Lys Leu Phe Ser His Ile Glu Ile Glu Lys Glu Asn Lys Gly Leu Glu
                115                 120                 125

Glu Thr Ile Pro Ser Lys Leu Leu Lys Tyr Leu Leu Gly Lys Asn Asp
130                 135                 140

Phe Tyr Lys Val Ile Ser Leu Glu Asn Thr Lys Ser Thr Met Val Gln
145                 150                 155                 160

Ala Phe Asn Leu Asn Gly Leu Leu Asn Gln Pro Cys Cys Asp Arg Lys
                165                 170                 175

Pro Glu Phe Lys Ile Gly Pro Lys Leu Lys Leu Pro Thr
                180                 185

<210> SEQ ID NO 37
<211> LENGTH: 189
<212> TYPE: PRT
<213> ORGANISM: Bacillus halodurans
<220> FEATURE:
<221> NAME/KEY: NON_CONS
<222> LOCATION: (49)..(50)
<220> FEATURE:
<221> NAME/KEY: NON_CONS
<222> LOCATION: (119)..(120)

<400> SEQUENCE: 37

Cys Val Leu Cys Ile Arg Arg Gln Asn Glu Trp Glu Ile Gly Leu Ser
1               5                   10                  15

Cys Lys His Asn His Thr Ala Val Lys His Ser Arg Leu Ser Arg Thr
                20                  25                  30

Ile Asp Phe Gly Asp Ser Trp Phe Gly Ile Pro Ser Ser Gln Asp Tyr
                35                  40                  45

Phe Pro Ile Val Asn Val Pro Gln Leu Ile Met Pro Thr Arg Phe Phe
50                  55                  60

Asp Ile Ser Phe Lys Arg Asp Ser Arg Asn Thr Ile Glu Val Thr Cys
65                  70                  75                  80

Asp Asn Gly Trp Thr Val Ser Leu Arg Ile His Asn Ala Ser Ser Arg
                85                  90                  95

Val Glu Pro Ser Leu Lys Phe Asp Val Arg Leu Thr Gly Val Pro Pro
                100                 105                 110

Tyr Leu His Thr His Phe Glu Leu Glu Arg Leu Asn Asn Asn Asn Pro
                115                 120                 125

Gly Leu Ile Pro Glu Arg Leu Leu Gln Tyr Leu Leu Gly Ser Asn Asp
130                 135                 140

```
Phe Tyr Lys Val Ile Thr His Asp Arg Arg Val Thr Gln Val Gln
145                 150                 155                 160

Ala Phe Asn Leu Tyr Gly Thr Leu Asn Arg Asn Ser Gly Arg Glu Arg
                165                 170                 175

Pro Ile Val Asn Val Pro Gln Leu Ile Met Pro Thr Arg
            180                 185
```

<210> SEQ ID NO 38
<211> LENGTH: 189
<212> TYPE: PRT
<213> ORGANISM: haemophilus influenzae
<220> FEATURE:
<221> NAME/KEY: NON_CONS
<222> LOCATION: (49)..(50)
<220> FEATURE:
<221> NAME/KEY: NON_CONS
<222> LOCATION: (119)..(120)

<400> SEQUENCE: 38

```
Cys Ile Leu Ile Gln Arg Glu Asn Ile Asn Trp Glu Ile Cys Leu Ser
1               5                   10                  15

Leu Lys His Asn His Phe Ala Val Lys His Ser Arg Leu Ser His Lys
                20                  25                  30

Ile Asp Phe Ser Glu Lys Trp Phe Gln Leu Pro Ser Ser Gln Asn Tyr
            35                  40                  45

Trp Ala Asp Ile Phe Ile Pro Val Ala Asn Leu Pro Thr Arg Ile Ile
    50                  55                  60

Asp Ile Asp Phe Lys Pro Asn Ser Lys Asn Thr Val Glu Leu Tyr Leu
65                  70                  75                  80

Asp Lys Gly Trp Gln Phe Ser Phe Arg Ile His Asn Ala Ser Thr Ile
                85                  90                  95

Ile Glu Pro Ser Leu Lys Phe Asp Ile Lys Leu Ile Gly Val Pro Ala
            100                 105                 110

Thr Ile Ile Cys Leu Glu Thr Ile Lys Glu Lys Tyr Asp Lys Tyr Asn
        115                 120                 125

Ser Ile Val Pro Gln Arg Met Val Glu Tyr Leu Leu Gly Tyr Phe Asp
130                 135                 140

Phe Tyr Lys Ile Ile Ser Gln Asp Asn Lys Lys Leu Thr Ser Ile Gln
145                 150                 155                 160

Ser Phe Asn Leu Arg Gly Thr Leu Asn Lys Pro Ser Lys Lys Arg Lys
                165                 170                 175

Ala Asp Ile Phe Ile Pro Val Ala Asn Leu Pro Thr Arg
            180                 185
```

<210> SEQ ID NO 39
<211> LENGTH: 189
<212> TYPE: PRT
<213> ORGANISM: Heliobacter acinoychis
<220> FEATURE:
<221> NAME/KEY: NON_CONS
<222> LOCATION: (49)..(50)
<220> FEATURE:
<221> NAME/KEY: NON_CONS
<222> LOCATION: (119)..(120)

<400> SEQUENCE: 39

```
Val Arg Asp Ile Leu Ile Tyr Phe Asp Arg Phe Cys Ile Gly Leu Ser
1               5                   10                  15

Ile Lys His Asn His Asp Ala Val Lys His Ser Arg Leu Ser Arg Asp
                20                  25                  30
```

```
Leu Asp Phe Gly Glu Lys Trp Leu Gly Val Gly Val Ser Gln Asn Tyr
            35                  40                  45

Lys Pro Lys Arg Ile Ile Pro Leu Ser Lys Leu Pro Thr Arg Met Ile
 50                  55                  60

His Phe Asp Phe Lys Pro Lys Ser Phe Asn Thr Leu Glu Leu Ile Leu
 65                  70                  75                  80

Asn Glu Gly Trp Ser Phe Ser Leu Arg Ile His Asn Ala Ser Ser Lys
                85                  90                  95

Val Glu Pro Ser Leu Lys Phe Asp Ile Lys Leu Leu Ala Ile Pro Val
            100                 105                 110

Ser Val Ala Val Phe Ile Thr Ile Leu Lys Ile Asp Glu Asn Lys Lys
            115                 120                 125

Asn Lys Ile Pro Gln Lys Met Val Gly Tyr Leu Leu Gly Lys Tyr Asp
 130                 135                 140

Phe Tyr Lys Ala Ile Leu Leu Glu Arg Glu Gln Lys Thr Lys Leu Glu
145                 150                 155                 160

Ala Tyr His Phe Asn Asn Thr Leu Asn Arg Ser Val Lys Asn Lys Pro
                165                 170                 175

Lys Arg Ile Ile Pro Leu Ser Lys Leu Pro Thr Arg Met
            180                 185

<210> SEQ ID NO 40
<211> LENGTH: 189
<212> TYPE: PRT
<213> ORGANISM: Clostridium thermocellum
<220> FEATURE:
<221> NAME/KEY: NON_CONS
<222> LOCATION: (49)..(50)
<220> FEATURE:
<221> NAME/KEY: NON_CONS
<222> LOCATION: (119)..(120)

<400> SEQUENCE: 40

Cys Ile Leu Cys Ile Arg Arg Gln Asn Glu Trp Glu Ile Gly Leu Ser
1                5                  10                  15

Cys Lys His Asn His Ala Ala Val Lys His Ser Arg Leu Ser Arg Thr
                20                  25                  30

Ile Asp Phe Gly Glu Leu Trp Phe Gly Ile Pro Cys Ser Glu Ser Tyr
            35                  40                  45

Phe Pro Leu Ile Asn Val Gln Gln Leu Pro Met Pro Thr Arg Phe Tyr
 50                  55                  60

Asn Ile Gly Phe Lys Pro Gly Ser Arg Asn Thr Val Leu Val Ala Leu
 65                  70                  75                  80

Asp Asn Gly Trp Thr Ile Ser Leu Arg Ile His Asn Ala Arg Thr Glu
                85                  90                  95

Val Glu Pro Ser Leu Lys Phe Asp Val Gln Leu Val Gly Val Pro Pro
            100                 105                 110

Leu Leu Tyr Ser His Phe Glu Leu Glu Arg Leu Asn Gln Asn Asn Gln
            115                 120                 125

Gly Val Ile Pro Glu Arg Leu Leu His Tyr Leu Leu Gly Arg Asn Asp
 130                 135                 140

Phe Tyr Lys Ile Ile Thr Ile Asp Asn Arg Arg Val Thr Gln Val Gln
145                 150                 155                 160

Ala Phe Asn Met Tyr Gly Thr Leu Asn Arg Asn Ala Gly Arg Glu Arg
                165                 170                 175

Pro Leu Ile Asn Val Gln Gln Leu Pro Met Pro Thr Arg
            180                 185
```

180                 185

<210> SEQ ID NO 41
<211> LENGTH: 189
<212> TYPE: PRT
<213> ORGANISM: Heliobacter pylori
<220> FEATURE:
<221> NAME/KEY: NON_CONS
<222> LOCATION: (49)..(50)
<220> FEATURE:
<221> NAME/KEY: NON_CONS
<222> LOCATION: (119)..(120)

<400> SEQUENCE: 41

Ile Arg Asp Ile Leu Ile Tyr Phe Asp Arg Phe Cys Ile Gly Leu Ser
1               5                   10                  15

Ile Lys His Asn His Asp Ala Val Lys His Ser Arg Leu Ser Lys Asp
            20                  25                  30

Leu Asp Phe Gly Lys Lys Trp Leu Gly Val Gly Val Ser Gln Asn Tyr
        35                  40                  45

Lys Pro Lys Arg Ile Ile Pro Leu Ser Lys Leu Pro Thr Arg Met Ile
50                  55                  60

Tyr Phe Asp Phe Lys Pro Lys Ser Phe Asn Thr Leu Glu Leu Val Leu
65                  70                  75                  80

Asp Glu Gly Trp Ser Phe Ser Leu Arg Ile His Asn Ala Ser Ser Arg
                85                  90                  95

Val Glu Pro Ser Leu Lys Phe Asp Ile Lys Leu Leu Ser Lys Pro Glu
            100                 105                 110

Ser Val Ala Val Phe Ile Val Val Leu Arg Ile Asp Glu Asn Lys Lys
        115                 120                 125

Asn Lys Val Pro Gln Lys Met Val Glu Tyr Leu Leu Gly Lys Tyr Asp
130                 135                 140

Phe Tyr Lys Ala Ile Leu Leu Glu Arg Glu Gln Lys Thr Lys Leu Glu
145                 150                 155                 160

Ala Tyr His Phe Asn Asn Thr Leu Asn Arg Ser Val Lys Asn Lys Pro
                165                 170                 175

Lys Arg Ile Ile Pro Leu Ser Lys Leu Pro Thr Arg Met
            180                 185

<210> SEQ ID NO 42
<211> LENGTH: 189
<212> TYPE: PRT
<213> ORGANISM: Bacteroides species 3_1_33FAA
<220> FEATURE:
<221> NAME/KEY: NON_CONS
<222> LOCATION: (49)..(50)
<220> FEATURE:
<221> NAME/KEY: NON_CONS
<222> LOCATION: (119)..(120)

<400> SEQUENCE: 42

Asp Ile Leu Ile Val Arg His Asn Ile Gln Trp Glu Ile Gly Leu Ser
1               5                   10                  15

Leu Lys His Asn His Phe Ala Val Lys His Ser Arg Leu Ser Gln Lys
            20                  25                  30

Leu Asp Phe Gly Ala Lys Trp Tyr Gly Ile Pro Cys Ser Gln Lys Tyr
        35                  40                  45

Trp Ala Ser Met Glu Ile Pro Ile Ala Ser Leu Pro Thr Arg Ile Val
50                  55                  60

Ser Leu Asp Phe Val Pro Asn Lys Ala Asn Thr Val Glu Leu Tyr Met

```
                65                  70                  75                  80
Asp Gly Gly Trp Gln Phe Ser Phe Arg Ile His Asn Ala Glu Lys Lys
                    85                  90                  95

Val Val Pro Ser Leu Lys Phe Asp Ile Gln Ile Val Gly Met Pro Thr
                100                 105                 110

Thr Ile Ile Thr Ile Asn Cys Glu Ile Asn Leu Gln Asn Gln Ile His
                115                 120                 125

Pro Asp Ile Pro Ser Arg Leu Val Glu Tyr Leu Leu Gly Lys His Asp
            130                 135                 140

Phe Tyr Lys Val Ile Ser Ile Asp Lys Gln Arg Thr Thr Gln Ile Gln
145                 150                 155                 160

Ser Tyr Asn Leu His Gly Thr Leu Asn Arg Asn Gly Thr Tyr Arg Lys
                165                 170                 175

Ala Ser Met Glu Ile Pro Ile Ala Ser Leu Pro Thr Arg
                180                 185

<210> SEQ ID NO 43
<211> LENGTH: 189
<212> TYPE: PRT
<213> ORGANISM: Streptobacillus moniliformis
<220> FEATURE:
<221> NAME/KEY: NON_CONS
<222> LOCATION: (49)..(50)
<220> FEATURE:
<221> NAME/KEY: NON_CONS
<222> LOCATION: (119)..(120)

<400> SEQUENCE: 43

Asp Leu Leu Ile Ile Arg Arg Gly Ile Lys Trp Glu Ile Gly Phe Ser
1               5                   10                  15

Val Lys His Asn His Phe Ala Val Lys His Ser Arg Leu Ser Lys Asn
                20                  25                  30

Ile Asp Phe Gly Lys Lys Trp Tyr Gly Ile Glu Cys Ser Lys Asn Tyr
            35                  40                  45

Trp Arg Asn Ile Glu Leu Lys Ile Ser Ser Leu Pro Thr Arg Ile Val
        50                  55                  60

Ser Leu Glu Tyr Lys Pro Lys Ser Lys Asn Thr Leu Glu Leu Tyr Leu
65                  70                  75                  80

Asp Arg Gly Trp Gln Phe Ser Phe Arg Ile His Asn Ala Ser Thr Lys
                85                  90                  95

Val Glu Thr Ser Leu Lys Phe Asp Ile Gln Ile Ile Gly Met Pro Thr
                100                 105                 110

Thr Ile Ile Ser Ile Asp Cys Phe Met Asn Glu Leu Ile Arg Gln Arg
            115                 120                 125

Glu Asp Ile Pro Lys Leu Met Val Glu Tyr Leu Leu Gly Lys Phe Asp
        130                 135                 140

Phe Tyr Lys Val Ile Gly Ile Asp Asn Lys Arg Ile Thr Gln Ile Gln
145                 150                 155                 160

Ser Tyr Asn Leu Arg Gly Ser Leu Asn Lys Gln Gly Lys Asn Arg Lys
                165                 170                 175

Arg Asn Ile Glu Leu Lys Ile Ser Ser Leu Pro Thr Arg
            180                 185

<210> SEQ ID NO 44
<211> LENGTH: 189
<212> TYPE: PRT
<213> ORGANISM: Prevotella ruminicola
<220> FEATURE:
```

```
<221> NAME/KEY: NON_CONS
<222> LOCATION: (49)..(50)
<220> FEATURE:
<221> NAME/KEY: NON_CONS
<222> LOCATION: (119)..(120)

<400> SEQUENCE: 44
```

| Asp | Ile | Leu | Ile | Ile | Arg | Asp | Ser | Val | Lys | Trp | Val | Ile | Gly | Ile | Ser |
|---|---|---|---|---|---|---|---|---|---|---|---|---|---|---|---|
| 1 | | | | 5 | | | | | 10 | | | | | 15 | |

Val Lys His Asn His Leu Ala Val Lys His Ser Arg Leu Ser Asn Val
            20                  25                  30

Leu Asp Phe Gly Asn Ser Trp Leu Gly Met Pro Cys Ser Lys Thr Tyr
        35                  40                  45

Trp Pro Ser Arg Lys Ile Pro Ile Ser Leu Leu Pro Thr Arg Ile Ile
50                  55                  60

Ser Phe Gly Leu Lys Pro Lys Ser Asn Asn Thr Ala Glu Leu Tyr Met
65                  70                  75                  80

Asp Asn Gly Trp Gln Phe Ser Phe Arg Ile His Asn Ala Ser Thr Leu
                85                  90                  95

Ile Glu Pro Ser Leu Lys Phe Asp Ile Gln Ile Ile Gly Met Pro Thr
            100                 105                 110

Ser Ile Ile Thr Ile Asn Cys Glu Ile Asn Lys Asp Tyr Glu Lys Asp
        115                 120                 125

Lys Thr Val Pro Ser Arg Met Val Glu Tyr Leu Leu Gly Lys Tyr Asp
130                 135                 140

Phe Tyr Lys Leu Ile Gly Ile Asp Ser Ser Lys Met Thr Gln Leu Met
145                 150                 155                 160

Ala Phe Asn Leu Arg Gly Thr Leu Asn His Ala Ser Lys Thr Lys Val
                165                 170                 175

Pro Ser Arg Lys Ile Pro Ile Ser Leu Leu Pro Thr Arg
            180                 185

```
<210> SEQ ID NO 45
<211> LENGTH: 189
<212> TYPE: PRT
<213> ORGANISM: Mobiluncus curtisii
<220> FEATURE:
<221> NAME/KEY: NON_CONS
<222> LOCATION: (49)..(50)
<220> FEATURE:
<221> NAME/KEY: NON_CONS
<222> LOCATION: (119)..(120)

<400> SEQUENCE: 45
```

Asp Ile Val Ile Lys Arg Asp Ala Ile Glu Trp Glu Ile Gly Leu Ser
1               5                   10                  15

Val Lys His Asn His Glu Ala Val Lys His Ser Arg Leu Ser His Lys
            20                  25                  30

Leu Asp Phe Gly Asn Glu Trp Phe Gly Ile Pro Cys Ser Gln Arg Tyr
        35                  40                  45

Trp Ala Thr Ile Ser Ala Pro Ile Val Glu Leu Pro Thr Glu Leu Val
50                  55                  60

Thr Leu Lys Phe Lys Gln Gly Ser Thr Asn Thr Val Glu Met Tyr Leu
65                  70                  75                  80

Asn Asn Gly Trp Gln Leu Ser Phe Arg Ile His Asn Ala Ser Ser Arg
                85                  90                  95

Val Glu Pro Ser Leu Lys Phe Asp Val Gln Phe Ile Gly Met Pro Val
            100                 105                 110

```
Ser Val Leu Thr Ile Glu Cys Glu Leu Tyr Arg Ala Tyr Thr Ala Asn
            115                 120                 125

Pro Asp Met Pro Arg Lys Met Val Glu Tyr Leu Ile Gly Thr Arg Asp
130                 135                 140

Tyr Tyr Lys Val Val Ser His Asp Arg Ser His Leu Thr Ile Ile Ser
145                 150                 155                 160

Thr Phe Asn Ile His Gly Thr Leu Asn Arg Pro Ser Ala Ile Thr Val
                165                 170                 175

Ala Thr Ile Ser Ala Pro Ile Val Glu Leu Pro Thr Glu
                180                 185

<210> SEQ ID NO 46
<211> LENGTH: 188
<212> TYPE: PRT
<213> ORGANISM: Bacteroides ovatus
<220> FEATURE:
<221> NAME/KEY: NON_CONS
<222> LOCATION: (49)..(50)
<220> FEATURE:
<221> NAME/KEY: NON_CONS
<222> LOCATION: (119)..(120)

<400> SEQUENCE: 46

Asp Ile Leu Ile Ile Arg His Asn Ile Gln Trp Glu Gly Leu Ser Leu
1               5                   10                  15

Lys His Asn His Phe Ala Val Lys His Ser Arg Leu Ser Arg Arg Leu
            20                  25                  30

Asp Phe Gly Lys Glu Trp Tyr Gly Ile Pro Cys Ser Gln Asp Tyr Trp
        35                  40                  45

Ala Ser Ile Gln Ile Pro Val Ala Cys Leu Pro Thr Arg Ile Val Ser
    50                  55                  60

Leu Gly Phe Val Pro Glu Arg Thr Asn Thr Val Glu Leu Tyr Met Asp
65                  70                  75                  80

Gly Gly Trp Gln Phe Ser Phe Arg Ile His Asn Ala Glu Thr Tyr Val
                85                  90                  95

Val Pro Thr Leu Lys Phe Asp Ile Gln Ile Val Gly Met Pro Thr Ala
            100                 105                 110

Ile Ile Thr Ile Asn Cys Glu Ile Asn Arg Gln Tyr Gln Val His Lys
        115                 120                 125

Asp Ile Pro Gly Lys Leu Val Glu Tyr Leu Leu Gly Lys His Asp Phe
    130                 135                 140

Tyr Lys Ile Ile Ser Ile Asp Lys Glu Gln Thr Thr Arg Ile Gln Ser
145                 150                 155                 160

Tyr Asn Leu His Gly Thr Leu Asn Gln Asn Ser Glu Ser Glu Gln Ala
                165                 170                 175

Ser Ile Gln Ile Pro Val Ala Cys Leu Pro Thr Arg
            180                 185

<210> SEQ ID NO 47
<211> LENGTH: 119
<212> TYPE: PRT
<213> ORGANISM: Bartonella grahamii
<220> FEATURE:
<221> NAME/KEY: NON_CONS
<222> LOCATION: (49)..(50)

<400> SEQUENCE: 47

Val Cys Asp Ile Ile Leu Lys Val Pro Glu Asn His Ile Gly Ile Ser
1               5                   10                  15
```

```
Ala Lys His Asn His Ser Ala Ile Lys His Pro His Leu Phe Gly Lys
            20                  25                  30

Ile Asp Phe Gly Lys Glu Trp Ala Gly Tyr Pro Cys Ser Ser Leu Tyr
        35                  40                  45

Phe Thr Leu Gly Tyr Gly Arg Lys Trp Lys Ile Pro Ser Lys Ile Leu
    50                  55                  60

Ser Val Ala Ile Lys Pro Glu Ser Lys Asn Lys Leu Ile Ile Ile Phe
65                  70                  75                  80

Glu Asp Gly Trp Ser Ile Ser Phe Arg Ile His Asn Ala Ser Ser Lys
                85                  90                  95

Val Glu Ala Phe Leu Lys Phe Asp Ile Gln Phe Val Gly Leu Ser Ser
            100                 105                 110

Gln Val Val Ser His Gln Ile
        115

<210> SEQ ID NO 48
<211> LENGTH: 49
<212> TYPE: PRT
<213> ORGANISM: unknown
<220> FEATURE:
<223> OTHER INFORMATION: bacteria GOS_4010239; Environmental sample
      Lake Gatun

<400> SEQUENCE: 48

Val Arg Asp Val Ile Leu Lys Leu Ser Gly Arg Glu Ile Gly Ile Ser
1               5                   10                  15

Cys Lys Thr Asn His Glu Ala Phe Lys His Pro Arg Leu Ser Gly Lys
            20                  25                  30

Ile Asp Phe Val Lys Gln Trp Gly Leu Gly Ala Gly Cys Gly Asp His
        35                  40                  45

Tyr

<210> SEQ ID NO 49
<211> LENGTH: 33
<212> TYPE: DNA
<213> ORGANISM: haemophilus influenzae

<400> SEQUENCE: 49
ggccagcaaa aggccaggaa ccgtaaaaag gcc                             33

<210> SEQ ID NO 50
<211> LENGTH: 33
<212> TYPE: DNA
<213> ORGANISM: Caldicellulosiruptor bescii

<400> SEQUENCE: 50
ggccagcaaa aggccaggaa ccgtaaaaag gcc                             33

<210> SEQ ID NO 51
<211> LENGTH: 25
<212> TYPE: PRT
<213> ORGANISM: Caldicellulosiruptor bescii
<220> FEATURE:
<221> NAME/KEY: NON_CONS
<222> LOCATION: (13)..(14)

<400> SEQUENCE: 51

Asn Arg Ile Thr Phe Ser Gly Thr Val Asp Ser Gly Gly Phe Ile Phe
1               5                   10                  15

Leu Asp Pro Pro Tyr Tyr Ser Thr Thr
            20                  25
```

```
<210> SEQ ID NO 52
<211> LENGTH: 25
<212> TYPE: PRT
<213> ORGANISM: Caldicellulosiruptor kristjanssonii
<220> FEATURE:
<221> NAME/KEY: NON_CONS
<222> LOCATION: (13)..(14)

<400> SEQUENCE: 52

Asn Arg Ile Thr Phe Ser Gly Thr Gly Asp Ser Gly Gly Phe Ile Phe
1               5                   10                  15

Leu Asp Pro Pro Tyr Tyr Ser Thr Thr
            20                  25

<210> SEQ ID NO 53
<211> LENGTH: 25
<212> TYPE: PRT
<213> ORGANISM: Caldicellulosiruptor hydrothermalis
<220> FEATURE:
<221> NAME/KEY: NON_CONS
<222> LOCATION: (13)..(14)

<400> SEQUENCE: 53

Asn Arg Ile Thr Phe Ser Gly Thr Val Asp Ser Gly Gly Phe Ile Phe
1               5                   10                  15

Leu Asp Pro Pro Tyr Tyr Ser Thr Thr
            20                  25

<210> SEQ ID NO 54
<211> LENGTH: 25
<212> TYPE: PRT
<213> ORGANISM: Anabaena variabilis
<220> FEATURE:
<221> NAME/KEY: NON_CONS
<222> LOCATION: (13)..(14)

<400> SEQUENCE: 54

Asn Arg Ile Thr Phe Ser Gly Thr Val Glu Ser Gly Gly Phe Ile Phe
1               5                   10                  15

Leu Asp Pro Pro Tyr Phe Ser Ala Thr
            20                  25
```